Figure 1:
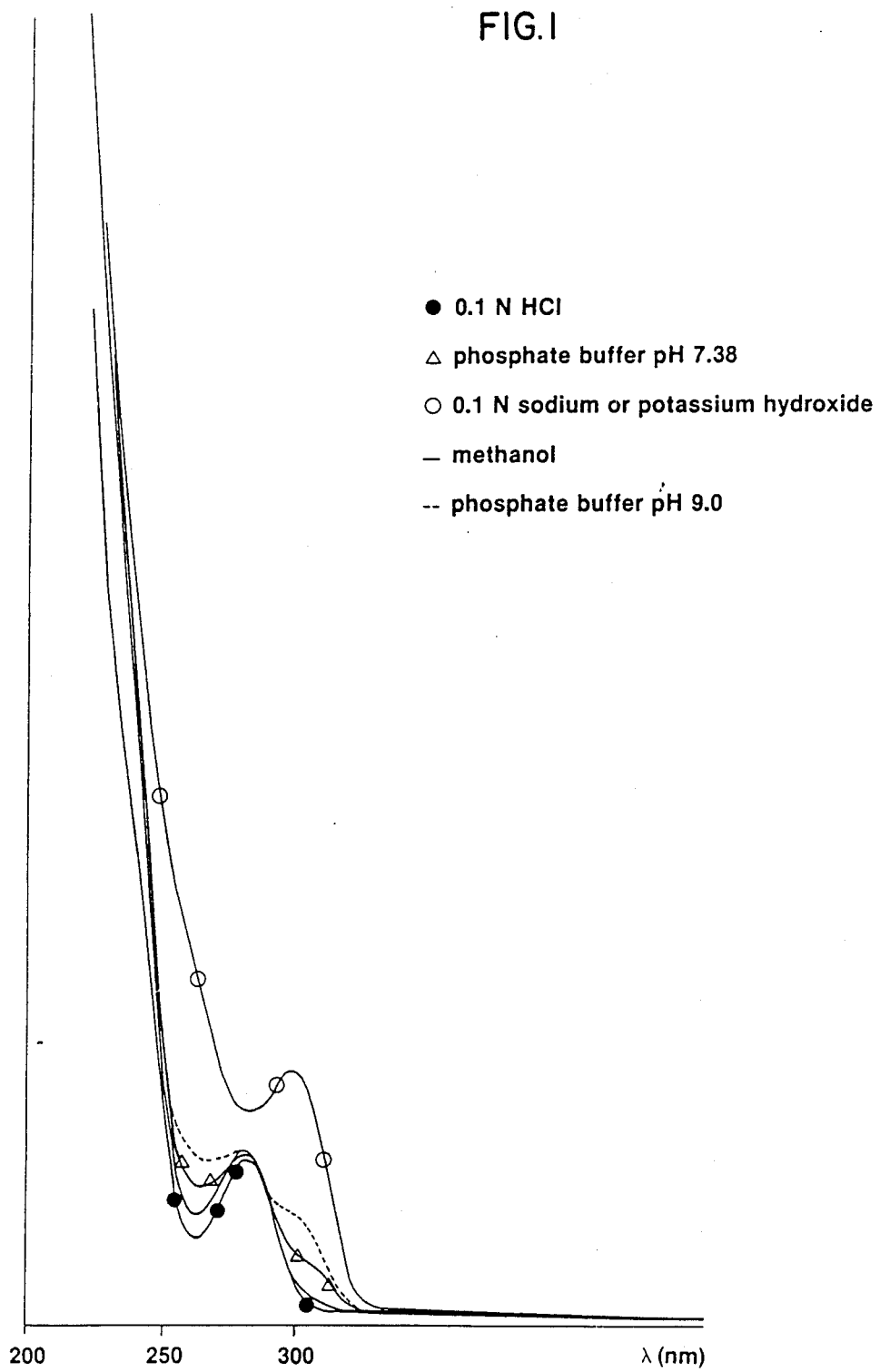

United States Patent [19]

Selva et al.

[11] Patent Number: 4,935,238
[45] Date of Patent: Jun. 19, 1990

[54] ANTIBIOTIC A 40926 COMPLEX AND ITS PURE FACTORS PA, PB, A, B AND $B_0$

[75] Inventors: Enrico Selva, Gropello Cairoli; Grazia Beretta, Milan; Luciano Gastaldo, Pogliano Milanese; Angelo Borghi; Beth P. Goldstein, both of Milan; Giovanni Cassani, Pavia; Vittorio Arioli, Cassina Rizzardi; Francesco Parenti, Milan, all of Italy

[73] Assignee: Gruppo Lepetit, S.p.A., Gerenzano, Italy

[21] Appl. No.: 785,930

[22] Filed: Oct. 9, 1985

[30] Foreign Application Priority Data

Oct. 11, 1984 [GB] United Kingdom ................. 8425685

[51] Int. Cl.$^5$ ........................ A61K 35/74; C12P 1/06; C12P 1/04
[52] U.S. Cl. ................................... 424/118; 424/119; 424/115; 435/169; 435/170
[58] Field of Search .................. 424/118, 115, 119; 435/169, 170

[56]     References Cited
         PUBLICATIONS

L. J. Nisbet, et al., Discovery, Comparative Antibacterial Activity and Structure Elucidation of AAJ-271, A Novel Group of Glycopeptides, Twenty-Sixth Interscience Conference on Antimicrobial Agents and Chemotherapy, Sep. 28–Oct. 1, 1986, New Orleans, La. abstract no. 226.

Primary Examiner—Jerome D. Goldberg

[57]     ABSTRACT

The present invention concerns a new antibiotic substance arbitrarily denominated antibiotic A 40926 complex and its factors antibiotic A 40926 factor A, antibiotic A 40926 factor B, antibiotic A 40926 factor $B_0$, antibiotic A 40926 factor PA and antibiotic A 40926 factor PB, a process for producing them by culturing the new strain Actinomadura sp. ATCC 39727 or an A 40926 producing variant or mutant thereof and the use of these new antibiotic substances in the treatment of infectious diseases involving microorganisms susceptible to them. The antibiotic substances of the invention are glycopeptidic substances belonging to the vancomycin class of antibiotics which have binding capacity to Acyl-D-Alanyl-D-Alanine.

16 Claims, 13 Drawing Sheets

× 0.1 N HCl

△ phosphate buffer pH 7.38

○ 0.1 N sodium or potassium hydroxide

— methanol

-- phosphate buffer pH 9.0

ANTIBIOTIC A 40926 COMPLEX AND ITS PURE FACTORS PA, PB, A, B AND $B_0$

The present invention concerns a new antibiotic substance arbitrarily denominated antibiotic A 40926 complex and its factors antibiotic A 40926 factor A, antibiotic A 40926 factor B, antibiotic A 40926 factor $B_0$, antibiotic A 40926 factor PA and antibiotic A 40926 factor PB, a process for producing them by culturing the new strain Actinomadura sp. ATCC 39727 or an A 40926 producing variant or mutant thereof and the use of these new antibiotic substances in the treatment of infectious diseases involving microorganisms susceptible to them.

The antibiotic substances of the invention are glycopeptidic substances belonging to the vancomycin class of antibiotics which have binding capacity to Acyl-D-Alanyl-D-Alanine.

Antibiotic A 40926 complex and its factors antibiotic A 40926 factor A, factor B, factor $B_0$, factor PA and factor PB, may form salts according to known per se techniques.

In the present description and claims the expression "antibiotic A 40926" as such represents a compound selected from antibiotic A 40926 complex, antibiotic A 40926 factor A, antibiotic A 40926 factor B, antibiotic A 40926 factor $B_0$, antibiotic A 40926 factor PA, antibiotic A 40926 factor PB a salt thereof or any mixture thereof. The expression "antibiotic A 40926 complex", "antibiotic A 40926 factor PA", "antibiotic A 40926 factor PB", "antibiotic A 40926 factor A", "antibiotic A 40926 factor B", antibiotic A 40926 factor $B_0$, when dealing with the biological properties, will encompass also the corresponding pharmaceutically acceptable salts.

Antibiotic A 40926 is produced by cultivating an Actinomadura strain isolated from a soil sample and which has been deposited on June 8, 1984 at the internationally recognized collection American Type Culture Collection (ATCC)—12301 Parklawn Drive, Rockville, Maryland 20852, U.S.A. under the provisions of the Budapest Treaty. The strain has been accorded the accession number ATCC 39727.

The producing strain was originally thought to belong to the genus Streptomyces and was initially denominated Streptomyces nov. sp. A 40926 and as such deposited with ATCC where it received the accession number ATCC 39727. Further studies, especially on cell-wall composition brought us to conclude that the new strain belongs to the genus Actinomadura. Accordingly, the strain originally deposited as Streptomyces sp. ATCC 39727 has been renamed Actinomadura sp. ATCC 39727.

The production of antibiotic A 40926 complex, antibiotic A 40926 factor A, factor B, factor $B_0$, factor PA or factor PB, is achieved by cultivating an Actinomadura sp. capable of producing it, i.e. Actinomadura sp. ATCC 39727 or an antibiotic A 40926-producing variant or mutant thereof, under aerobic conditions in an aqueous nutrient medium containing assimilable sources of carbon, nitrogen, and inorganic salts. Many of the nutrient media usually employed in the fermentation art, can be used, however certain media are preferred. Preferred carbon sources are glucose, mannose, galactose, starch, corn meal and the like. Preferred nitrogen sources are ammonia, nitrates, soybean meal, peptone, meat extract, yeast extract, tryptone, aminoacids, and the like. Among the inorganic salts which can be incorporated in the culture media there are the customary soluble salts capable of yielding sodium, potassium, iron, zinc, cobalt, magnesium, calcium, ammonium, chloride, carbonate sulfate, phosphate, nitrate and the like ions.

Ordinarily, the antibiotic-producing strain is pre-cultured in a shake flask, then the culture is used to inoculate jar fermentors for production of substantial quantities of the antibiotic substances. The medium used for the pre-culture can be the same as that employed for larger fermentations, but other media can also be employed. The antibiotic A 40926 producing-strain can be grown at temperatures between 20° and 40° C., preferably between 24° and 35° C. During fermentation, the antibiotic production can be monitored by testing broth or mycelial extract samples for antibiotic activity for instance by bioassays or TLC or HPLC procedures.

Sensitive organisms to antibiotics A 40926 such as *Bacillus subtilis* and *S. aureus* can be used as test organisms. The bioassay is conveniently performed by the agar diffusion method on agar plates. Maximum production of antibiotic activity generally occurs between the second and the fifth day of fermentation.

Antibiotic A 40926 is produced by cultivating the strain Actinomadura sp. ATCC 39727, or an antibiotic A 40926 producing mutant or variant thereof, and is mainly found in the culture broths.

The characteristics of Actinomadura sp. A 40926 ATCC 39727 are given in the following paragraphs:

MACROSCOPIC AND MICROSCOPIC EXAMINATION

The vegetative mycelium is composed of flexuous and branched hyphae (about 0.8 $\mu$m of diameter) which on some media, identified by an asterisk in Table I, slightly tends to fragment into rod-like elements after several days of growth, while on glucose-asparagine medium it fragments into coccoid elements.

Characteristic of this strain is the Burgundy color of the vegetative mycelium on some media.

The aerial mycelium is present only in few media; in particular, among those listed in Table I, it is present only in oatmeal agar and soil agar. On these media the aerial mycelium is white-grey and forms sphorophores arranged in hooks and short spirals of about 10 to 20 spores.

The spores are cylindrical and have an average size of $0.8 \times 1.2$ $\mu$m.

DETERMINATION OF GROWTH CHARACTERISTICS

For the examination of the cultural characteristics, Actinomadura sp. ATCC 39727 was cultivated on various standard media suggested by Shirling and Gottlieb (Shirling E. B. and Gottlieb D., 1966—Method for characterization of Streptomyces species—Int. J. Syst. Bacteriol, 16, 313-340) with the addition of several media recommended by Waksman (Waksman, S. A. 1961—The Actinomycetes—The Williams and Wilkins Co. Baltimore; Vol. 2, 328-334). Color determination was made whenever necessary by the method of Maerz and Paul (Maerz A. and M. Rea Paul, 1950—A Dictionary of Color—2nd Edition McGraw-Hill Book Company Inc. New York).

The ability of the organism to utilize different carbon sources was investigated by the method described by Shirling and Gottlieb.

The cultural and physiological characteristics and the carbon sources utilization are reported in Tables I, II, III.

The readings in Table I have been taken after two weeks incubation at 28° C.

TABLE I
CULTURAL CHARACTERISTICS OF STRAIN
Actinomadura sp. ATCC 39727

| Culture media | Characteristics |
| --- | --- |
| Medium No. 2 (yeast extract - malt agar) | Abundant growth, with crusty surface, 8/L/8, traces of amber-pink soluble pigment |
| Medium No. 3 (oatmeal agar) | Abundant growth, with smooth surface, violet, 55/E/4, aerial mycelium very scant grey, soluble pigment violet 55/H/4 |
| Medium No. 4 (inorganic salts-starch agar) | Moderate growth, with smooth and thin surface, cream 10/D/2 |
| Medium No. 5 (glycerol-asparagine agar) | Moderate growth, with smooth and thin surface, apricot 10/B/2 |
| Medium No. 6* (peptone-yeast extract iron agar) | Moderate growth, with slightly crusty surface, amber 12/D/9 |
| Medium No. 7 (tyrosine agar) | Abundant growth, with smooth and thin surface, amber-brown 13/K/12 |
| Oatmeal agar* | Abundant growth, with smooth surface, Burgundy 8/L/7, aerial mycelium, moderate light yellow-grey 44/B/2 |
| Hickey and* Tresner's agar | Abundant growth, with wrinkled surface, amber-brown 13/K/12 |
| Czapeck glucose agar | Moderate growth, with smooth surface, light-yellow 9/I/3 |
| Glucose asparagine* agar | Scant growth, with creamy surface, straw-yellow 9/E/1 |
| Nutrient agar | Abundant growth, with wrinkled surface, light-orange 11/C/7 |
| Potato agar* | Abundant growth, with wrinkled surface, Burgundy 8/L/9 |
| Bennett's agar* | Abundant growth, with crusty surface, Burgundy 8/L/8, soluble pigment deep amber rose 5/J/10 |
| Calcium malate agar | Moderate growth, with smooth surface, apricot 10/B/3 |
| Skim milk agar | Abundant growth, with slightly wrinkled surface, orange 9/B/9 |
| Czapeck sucrose agar | Abundant growth, with smooth surface, apricot 10/B/6 |
| Egg albumin agar* | Abundant growth, with smooth surface, rose 52/B/3, traces of a soluble pigment, rose 52/B/3 |
| Sabouraud agar | No growth |
| Soil agar | Scant growth, colorless, white-grey aerial mycelium |
| Dextrose triptone agar* | Moderate growth, with smooth and thin surface, light-yellow 10/G/2 |
| Potato plug | Abundant growth, orange-brown, traces of white-grey aerial mycelium |

PHYSIOLOGICAL CHARACTERISTICS
TABLE II

| Tests | Physiological characteristics Results |
| --- | --- |
| Starch hydrolysis | negative |
| H₂S formation | negative on Medium No. 6 |

TABLE II-continued

| Tests | Physiological characteristics Results |
| --- | --- |
| | positive with lead acetate strips |
| Tyrosine reaction | positive |
| Casein hydrolysis | positive |
| Calcium malate hydrolysis | negative |
| Gelatin liquefaction | positive |
| Litmus milk — coagulation | negative |
| Litmus milk — peptonization | positive |
| Cellulose decomposition | negative |
| Nitrate reduction | positive |

UTILIZATION OF CARBON SOURCES
TABLE III

| Carbon Source | Carbon Utilization Growth |
| --- | --- |
| Arabinose | + |
| Xylose | + |
| Mannose | + |
| Fructose | + |
| Raffinose | + |
| Rhamnose | + |
| Glucose | + |
| Lactose | + |
| Galactose | + |
| Inositol | − |
| Sucrose | + |
| Cellulose | − |
| Salicin | + |
| Mannitol | + |
| Ribose | − |

+ = growth
− = no growth

CHEMOTAXONOMICAL CHARACTERISTICS

Cell Wall Analysis

The analysis of aminoacids present in the cell wall was carried out by the methods described in the work of Becker et al., "Rapid differentiation between Nocardia and Streptomyces by paper chromatography of whole cell hydrolysates", Appl. Microbiol. 12, 421–423 (1964). The analysis of the whole cell hydrolyzed revealed the presence of meso-diaminopimelic acid.

The analysis of pure cell wall, obtained with the method of Kawamoto et al. (I. Kawamoto, T. Oka, and T. Nara, "Cell-wall composition of *Micromonospora olivoasterospora*, *Micromonospora sagamiensis*, and related organism", J. of Bacteriology 146, 527–534, 1981) showed absence of glycine.

Sugar Analysis

The analysis of sugar content was carried out by the method of M. P. Lechevalier, "Identification of aerobic actinomycetes of clinical importance", J. Lab. Clin. Med. 71, 934–944 (1968) using thin layer chromatography cellulose sheets as described by J. L. Staneck and G. D. Roberts, "Simplified approach to identification of aerobic actinomicetes by thin-layer chromatography", 28, 226–231 (1974) with the following solvent system: Ethylacetate-Pyridine-Water (100:35:25 by volume). The obtained results showed the presence of mainly glucose and ribose while lower quantities of galactose, mannose and madurose (3-O-methyl-D-galactose) were also detected.

Mycolic Acids

An assay for detecting the presence of mycolic acids was carried out by the following method of Minnikin et al. (D. E. Minnikin, L. Alshamaony and M. Goodfellow, "Differentiation of Mycobacterium, Nocardia and related taxa by thin layer chromatography analysis of whole organism methanolysates", Journal of General Microbiology 88, 200–204, 1975).

The results of the assay were negative: mycolic acids were not found.

Identity of the Strain

The strain is assigned to the Actinomycetes genus Actinomadura because of the presence of meso-diaminopimelic acid and madurose, the lack of glycine in the peptodoglycan, the lack of mycolic acids and the formation of aerial mycelium with moderately long spore chains.

As with other microorganisms, the characteristics of the A 40926 producing strain are subject to variation. For example, artificial variants and mutants of the strain can be obtained by treatment with various known mutagens, such as U.V. rays, X-rays, high frequency waves, radioactive rays, and chemicals such as nitrous acid, N-methyl-N'-nitro-N-nitrosoguanidine, and many others. All natural and artificial variants and mutants which belong to the species of the genus Actinomadura and produce A 40926 antibiotics, are deemed equivalent to strain Actinomadura sp. ATCC 39727 and are contemplated to be within the scope of this invention.

The recovery of the antibiotic substances of the invention from the fermentation broths of the producing microorganism is conducted according to known per se techniques which include extraction with solvents, precipitation by adding non-solvents or by changing the pH of the solution, partition chromatography, reverse-phase partition chromatography, ion-exchange chromatography, affinity chromatography and the like.

A preferred procedure includes an affinity chromatography on immobilized D-Alanyl-D-Alanine followed by reverse-phase column chromatography.

Immobilized D-Alanyl-D-Alanine matrices suitable for the present recovery process are disclosed in European Patent Application No. 83112555. The preferred matrix in the present process is D-Alanyl-D-alanine coupled with a controlled pore cross-linked polydextrane.

The fermentation broth can be subjected to the affinity chromatography directly after filtration or after a preliminary purification procedure. This latter procedure includes making the whole fermentation mass basic, preferably between pH 8.5 and 10.5, in order to solubilize the antibiotic substance adsorbed on the mycelium and then filtering. The clear filtrate is brought to pH 2.5–4.5 and filtered again in the presence of a filter aid. This filtrate is discarded while the recovered filtration cake is suspended in water, made basic, preferably at a pH between 8 and 9, and filtered. The filtration cake is re-subjected to the same procedure while the filtrates, which contain antibiotic A 40926, are pooled.

These filtrates or the filtered fermentation broths are then subjected to an affinity chromatography on immobilized D-Alanyl-D-Alanine, either in column or batchwise.

The binding of the antibiotic substance to the affinity matrix is preferably made at a pH of about 7.0–8.0 and its elution is performed at more basic pH values (preferably between 9.0 and 10.5) by means of an aqueous base. This aqueous base may be ammonia, a volatile amine, an alkali or alkali metal hydroxide or a basic buffered solution optionally in the presence of a polar organic solvent such as a polar water-miscible solvent as defined below.

After removing the impurities by rinsing the column with aqueous buffer pH 4–8, optionally containing salts, urea and/or water miscible solvents, the antibiotic A 40926 is eluted with the above eluting mixture. The crude antibiotic substance is then recovered preferably by removing water from the pooled antibiotic-containing fractions by azeotropical distillation with an organic solvent capable of forming minimum azeotropic mixtures with water, followed by addition of a non-solvent to precipitate the desired product.

Representative examples of organic solvents capable of forming minimum azeotropic mixtures with water are n-butanol, benzene, toluene, butyl ether, carbon tetrachloride, chloroform, cyclohexane, 2,5-dimethylfurane, hexane and m-xilene; the preferred solvent being n-butanol.

Examples of non-solvents are: petroleum ether, lower alkyl ethers, such as ethyl ether, propyl ether and butyl ether, and lower alkyl ketones such as acetone. Alternatively, the pooled antibiotic-containing fractions are concentrated to a small volume, preferably by azeotropical distillation with an organic solvent defined as above, and the resulting aqueous solution is lyophilized.

If the aqueous base employed in the elution is unvolatile, it may be necessary to neutralize and desalt the concentrate before precipitation or freeze-drying.

A convenient desalting procedure includes applying the antibiotic containing aqueous solution to a silanized silica gel column, washing with distilled water and eluting with a mixture of a polar water-miscible solvent and water.

Representative examples of polar water-miscible solvents are: water-soluble alcohols, (such as methanol, ethanol, iso-propanol, n-butanol), acetone, acetonitrile, lower alkyl alkanoates (such as ethyl acetate), tetrahydrofuran, dioxane and dimethylformamide and mixtures thereof; the preferred polar water-miscible solvent being acetonitrile.

Alternatively, desalting may be carried out by applying the antibiotic containing solution to the above described affinity column, washing with distilled water and eluting with a volatile aqueous base as described above for the elution of the affinity chromatography. The product so obtained is antibiotic A 40926 complex. If necessary, it may be further purified or subjected as such to the separation of its factors A, B, $B_0$, PA and PB.

A convenient procedure to obtain a pure antibiotic A 40926 complex is represented by a further purification of the complex as obtained above on an affinity chromatography column. The same stationary phase as above (immobilized D-Alanyl-D-Alanine) is generally used and the desired antibiotic substance is eluted by following the affinity chromatography procedure on immobilized D-Alanyl-D-Alanine described above. A preferred immobilized D-Alanyl-D-Alanine is Sepharose-ϵ-aminocaproyl-D-Alanyl-D-Alanine, a preferred equilibrating mixture is 0.16% (w/v) ammonia containing 2M NaCl adjusted to pH 7–8, a preferred rinsing solution is 0.16% (w/v) ammonia containing 2M NaCl adjusted to pH 8–9.5, a preferred eluting mixture is 0.16% (w/v) ammonia containing 2M NaCl adjusted to pH 10.5–12 and a most preferred eluting mixture is the above mixture adjusted to pH 11.5.

The antibiotic A 40926 factors, namely antibiotic A 40926 factor A, antibiotic A 40926 factor B, antibiotic A 40926 factor $B_0$, antibiotic A 40926 factor PA and antibiotic A 40926 factor PB are isolated from an aqueous solution of antibiotic A 40926 complex by column chromatography and preferably by reverse-phase column chromatography. The preferred stationary phase in the case of reverse-phase column chromatography is silanized silica gel. Good results may be obtained however also with column chromatography on non-functionalized polystyrene and acrylic resins such as those sold under the trade names Amberlite XAD-2, XAD-4, XAD-7 and XAD-8 (Rohm and Haas) or Diaion HP 20 (Mitsubishi). In case the reverse-phase purification step is accomplished by means of a silanized silica gel as the stationary phase, the column is preferably pre-equilibrated with a buffered aqueous solution at pH between 4 and 9 and preferably between 5.5–6.5 and then eluted with a linear gradient of a polar water-miscible solvent in the same buffered solution. Representative examples of polar water-miscible solvents are: water-soluble alcohols, (such as methanol, ethanol, iso-propanol, n-butanol), acetone, acetonitrile, tetrahydrofuran, dioxane and dimethylformamide and mixtures thereof; the preferred polar water-miscible solvent being acetonitrile.

The eluted fractions are assayed for their antibiotic content by means of the usual bioassays, such as paper-disc or agar-diffusion assays, on susceptible microorganisms. Examples of susceptible organisms are *Bacillus subtilis* and *S. aureus*.

The chromatography is also conveniently monitored by TLC or HPLC techniques.

A preferred HPLC technique is represented by a reverse-phase HPLC using a column of porous and spheric particles of silanized silica gel functionalized with C-18 alkyl groups having a diameter preferably of 5 micrometers (such as 5 μm Ultrasphere ® ODS Altex; Beckman Co.), a pre-column which is a silica gel functionalized with C-18 alkyl groups (such as RP 18 Brownlee Labs) and an eluent which is a linear gradient mixture of a polar water miscible solvent, such as one of those described above, in an aqueous buffered solution.

Preferably this solution is adjusted to pH 5–7. A most preferred eluent is represented by a linear gradient from 5 to 60% of eluent B in eluent A wherein eluent A is a mixture of acetonitrile/aqueous buffer, pH 5–7, 10:90 and eluent B is a mixture of acetonitrile/aqueous buffer, pH 5–7, 70:30. As known in the art, many substances can be used as internal standards. A very convenient one is, in this case, Teicoplanin $A_2$ component 2 (Gruppo Lepetit S.p.A.) which has a retention time close to the compounds of the invention in this HPLC system. This standard substance is known and has been described in GB-A-2121401.

Fractions with a similar antibiotic content are pooled and desalted as described above to give essentially pure antibiotic A 40926 factor A, factor B, factor $B_0$, factor PA, and factor PB.

Essentially pure antibiotic A 40926 factor A and antibiotic A 40926 factor B, antibiotic A 40926 factor $B_0$, antibiotic A 40926 factor PA and antibiotic A 40926 factor PB are obtained from those fractions containing them by a variety of known techniques such as lyophilization, precipitation by non-solvents or precipitation by changing the pH of the aqueous solution.

A convenient procedure includes adding a solvent capable of forming azeotropic mixtures with water, removing water by azeotropic distillation and then collecting by filtration the precipitate obtained after addition of a non-solvent like those described above.

Antibiotic A 40926 factors PA and PB, at least under certain fermentation conditions, are the main antibiotic products of the A 40926 producing microorganism. Antibiotic A 40926 factors A and B are mainly transformation products of antibiotic A 40926 factor PA and factor PB respectively, and are often already present in the fermentation broth.

It has been found in fact that antibiotic A 40926 factor PA can be transformed into antibiotic A 40926 factor A and antibiotic A 40926 factor PB can be transformed into antibiotic A 40926 factor B under basic conditions. For instance, antibiotic A 40926 factor PA and antibiotic A 40926 factor PB are transformed into antibiotic A 40926 factor A and factor B respectively, by treatment with 0.5–10% aqueous ammonia or other nucleophilic base such as an organic amine at room temperature for 8–24 hours.

As a consequence, when the fermentation broth, or an antibiotic A 40926 containing extract or concentrate thereof, is allowed to stand for a certain time under basic conditions (e.g. aqueous solution of a nucleophilic base, at a pH>9 overnight,) an antibiotic A 40926 complex will be obtained which is enriched in antibiotic A 40926 factor A and factor B. If the period of exposure of the fermentation broth, extract or concentrate thereof, to a basic environment is short, an antibiotic A 40926 complex is obtained which is enriched in antibiotic A 40926 factor PA and factor PB.

A preferred procedure to obtain an antibiotic A 40926 complex enriched in factor A and factor B includes therefore leaving a solution of antibiotic A 40926 complex (which contains mainly antibiotic A 40926 factors PA and PB) at room temperature for 8–12 h in an aqueous nucleophilic base, such as aqueous ammonia, and then isolating the desired antibiotic complex as described above.

Examples of A 40926 containing solutions are fermentation broths, extracts and affinity chromatography eluted fractions.

Pure antibiotic A 40926 may be obtained by further purifying the crude complex by affinity chromatography as described above.

The product so obtained which possesses biological and physico-chemical properties derivable from the pure factors thereof, will be referred to in the examples as antibiotic A 40926 complex AB.

A preferred procedure to enrich in factors PA and PB an antibiotic A 40926 complex preparation, includes rapidly neutralizing the affinity chromatography eluted fractions with an acid, preferably a mineral acid such as sulfuric or hydrochloric acid.

The isolation of pure antibiotic A 40926 factors PA and PB from this complex can be achieved according to one of the above reported procedures.

A preferred procedure includes reverse-phase liquid chromatography, preferably in stainless steel colums under moderate pressure (5–50 bar) or at high pressure (100–200 bar) The solid phase may be a silanized silica gel with a hydrocarbon phase at (2–18) carbon atoms (most preferably C 18) or phenyl group, and the eluent is a mixture of a polar water-miscible solvent as defined above and an aqueous buffer at a pH compatible with the resin (preferably pH 4–8).

The elution is monitored as usual, the fractions having homogeneous antibiotic content are pooled and treated as described above to isolate the pure compounds having the characteristics reported below.

Sophisticated HPLC analysis has shown that antibiotic A 40926 factor B actually is a mixture of two factors denominated factor $B_0$ and factor $B_1$.

Antibiotic A 40926 factor $B_0$, which accounts for approximately 90% of antibiotic A 40926 factor B, is the factor that has $R_t$ of 1.22 relative to Teicoplanin $A_2$ component 2 in the system described below under point D of the physico-chemical characteristics of factor B, while factor $B_1$, which accounts for approximately 10% of antibiotic A 40926 factor B, is that with relative $R_t$ of 1.27 in the same system.

Pure antibiotic A 40926 factor $B_0$ is obtained by futher purification of antibiotic A 40926 factor B for instance by repeating the reverse-phase chromatography procedure used for its isolation.

The physico-chemical and biological properties of antibiotic A 40926 factor $B_0$ are substantially identical to those of antibiotic A 40926 factor B except that at the HPLC analysis in a system like the above cited one, it has only one peak ($R_t$ 1.22 relative to Teicoplanin $A_2$ component 2 in the described HPLC system).

Because of the above outlined similarities between antibiotic A 40926 factor B and antibiotic A 40926 factor $B_0$ in the present disclosure and claims the reference to the biological properties of antibiotic A 40926 factor B is to be understood as referring also to antibiotic A 40926 factor $B_0$ which is the main component (about 90%) of antibiotic A 40926 factor B and mainly contributes to its biological properties.

Alternatively, the antibiotic substances of the invention may be isolated from the fermentation broth or further purified by means of strong or weak anion resins including functionalized polystyrene, acrylic or polydextrane matrices. Examples of weak anion exchange resins are those sold under the following trade-names: Dowex MWA-1 or WGR (Dow Chemical), Amberlite IRA-73 (Rohm and Haas), DEAE-Sephadex (Pharmacia). Examples of strong anion exchange resins which may be used according to invention include those sold under the following trade names: Dowex MSA-1, SBR, SBR-P (Dow Chemical), Amberlite IR-904 (Rohm and Haas) and QAE-Sephadex (Pharmacia).

The elution of the antibiotic substances of the invention from these resins is conducted by means of linear gradient mixtures of aqueous solution of electrolytes, such as sodium or potassium hydrochlorides, in water or mixtures of water and an organic water-miscible solvent such as a lower alcohol (e.g. ($C_1$–$C_4$)alkanol) or lower alkyl ketones (e.g. acetone).

As already said, the antibiotic substances of the invention posses acid and basic functions and can form salts according to conventional procedures. Representative and suitable acid addition salts of the compounds of formula I include those salts formed by standard reaction with both organic and inorganic acids such as, for example, hydrochloric, hydrobromic, sulfuric, phosphoric, acetic trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like acids.

Representative examples of these bases are: alkali metal or alkaline-earth metal hydroxide such sodium, potassium, and calcium, hydroxide; ammonia and organic amines aliphatic, alicyclic or aromatic such as methylamine, dimethylamine, trimethylamine, and picoline.

The transformation of the free amino or non-salt compounds of the invention into the corresponding addition salts, and the reverse, i.e. the transformation of an addition salt of a compound of the invention into the non-salt or free amino form, are within the ordinary technical skill and are encompassed by the present invention.

For instance, a compound of the invention can be transformed into the corresponding acid or base addition-salt by dissolving the non-salt form in an aqueous solvent and adding a slight molar excess of the selected acid or base. The resulting solution or suspension is then lyophilized to recover the desired salt.

In case the final salt is unsoluble in a solvent where the non-salt form is soluble it is recovered by filtration from the organic solution of the non-salt form after addition of the stoichometric amount or a slight molar excess of the selected acid or base. The non-salt form can be prepared from a corresponding acid or base salt dissolved in an aqueous solvent which is then neutralized to free the non-salt form.

When following the neutralization desalting is necessary, a common desalting procedure may be employed. For example, column chromatography on silanized silica gel, non-functionalized polystyrene, acrylic and controlled pore polydextrane resins (such as Sephadex LH 20) or activated carbon may be conveniently used. After eluting the undesired salts with an aqueous solution, the desired product is eluted by means of a linear gradient or a step-gradient of a mixture of water and a polar or apolar organic solvent, such as acetonitrile/water from 50:50 to about 100% acetonitrile.

As it is known in the art, the salt formation either with pharmaceutically acceptable acids (bases) or non-pharmaceutically acceptable acids (bases) may be used as a convenient purification technique. After formation and isolation, the salt form of an A 40926 antibiotic can be transformed into the corresponding non-salt or into a pharmaceutically acceptable salt.

In some instances, the base addition salt of a compound of the invention is more soluble in water and hydrophilic solvents.

PHYSICO-CHEMICAL CHARACTERISTICS OF ANTIBIOTIC A 40926 FACTOR A (A) ultraviolet absorption spectrum, which is shown in FIG. 1 of the accompanying drawings, and exhibits the following absorption maxima:

|  | λ max (nm) |
|---|---|
| (a) 0.1 N HCl | 281 |
| (b) phosphate buffer pH 7.38 | 281 |
|  | 300 (shoulder) |
| (c) 0.1 N sodium or potassium hydroxide | 300 |
| (d) methanol | 282 |
| (e) phosphate buffer pH 9.0 | 282 |
|  | 300 (shoulder) |

Figure 2:
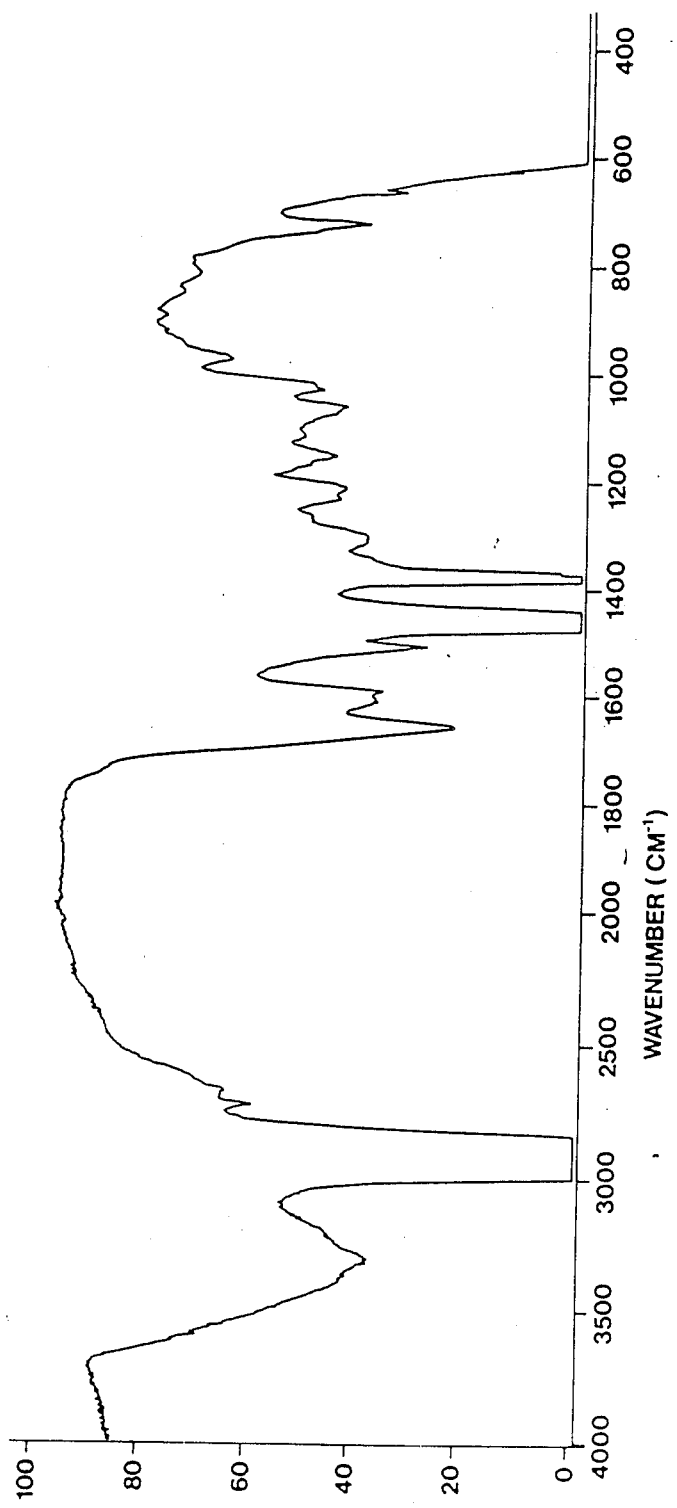

(B) infrared absorption spectrum which is shown in FIG. 2 of the accompanying drawings and exhibits the following absorption maxima (cm$^{-1}$): 3700–3100, 3100–2800 (nujol); 1655; 1620–1560; 1510; 1480–1410 (nujol); 1375 (nujol); 1320–1250; 1250–1190; 1100–950; 845; 810; 720 (nujol).

Figure 3:
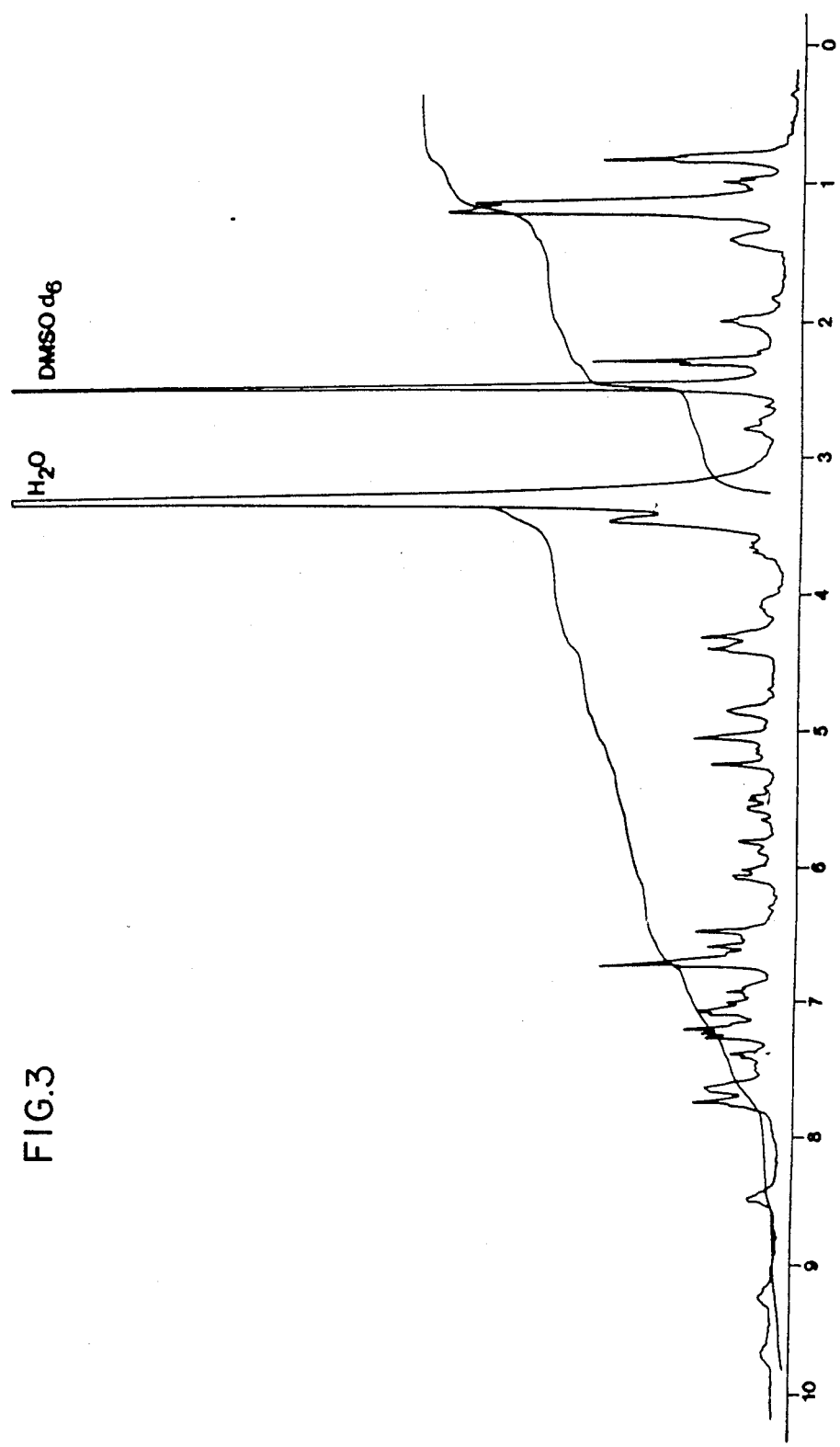

(C) $^1$H-NMR spectrum which is shown in FIG. 3 and exhibits the following groups of signals (in ppm) at 270 MHz recorded in DMSO d$_6$ (hexadeuterodimethylsulfoxide) using TMS as the internal standard (0.00 ppm), ($\delta$=ppm): $\delta$ 0.86 (t's, 6H); 1.21 ($\sim$11H); 1.43 (2H); 2.01 (2H); 2.31–2.34 (3H); 4–6.2 ($\sim$16H); 6.2–8 ($\sim$23H); 8.44, 9.22, 9.66 (broad bands; mobile protons) 2.5–4: interference from H$_2$O peaks.

(D) retention-time (R$_t$) of 1.22 relative to Teicoplanin A$_2$ component 2 (R$_t$=20.3 min), when analyzed by reverse phase HPLC under the following conditions:

| column: | Ultrasphere ODS (5 $\mu$m) Altex (Beckman) 4.6 mm (i.d.) × 250 mm |
|---|---|
| pre-column: | Brownlee Labs RP 18 (5 $\mu$m) |
| eluent A: | CH$_3$CN 10% } adjusted |
|  | (2.5 g/l) NaH$_2$PO$_4$.H$_2$O 90% } at pH 6.0 |
| eluent B: | CH$_3$CN 70% } adjusted |
|  | (2.5 g/l) NaH$_2$PO$_4$.H$_2$O 30% } at pH 6.0 |
| elution: | linear gradient from 5% to 60% of eluent B in eluent A, in 40 min |
| flow rate: | 1.8 ml/min |
| U.V. detector: | 254 nm |
| internal standard: | Teicoplanin A$_2$ component 2 (Gruppo Lepetit S.p.A.) |

Under the same conditions the retention time relative to Testosterone (Roussel Uclaf) is 0.60.

(E) elemental analysis, after the sample has been previously dried at about 140° C. under inert atmosphere ($\Delta$w 4.6%) which indicates the following approximate percentage composition (average): carbon 55.82%; hydrogen 5.17%; nitrogen 6.31%; chlorine (total) 4.24%; chlorine (ionic) 0.37%. Inorganic residue at 900° C. in the air: 1.2%.

(F) acid-base titration profile in 2-methoxyethanol (MCS): water, 4:1 upon titration with KOH after addition of an excess of HCl which indicates four ionizable functions having the following pk$_{MCS}$: 4.6, 5.6, 7.2, 9.2.

(G) R$_f$ value of 0.24 and a R$_f$ value relative to Teicoplanin A$_2$ component 2 of 0.70 in the following chromatographic system:

| 5% (w/v) aqueous Na$_2$SO$_4$ | 70 |
|---|---|
| acetonitrile | 30 | using silanized silica gel 60 F$_{254}$ Merck plates (layer thickness 0.25 mm)

Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using B. subtilis ATCC 6633 on minimal Davis medium.

(H) MW of about 1716 desumed from a FAB-MS spectrum showing the M+H$^\oplus$ peak at 1717.

Figure 4:
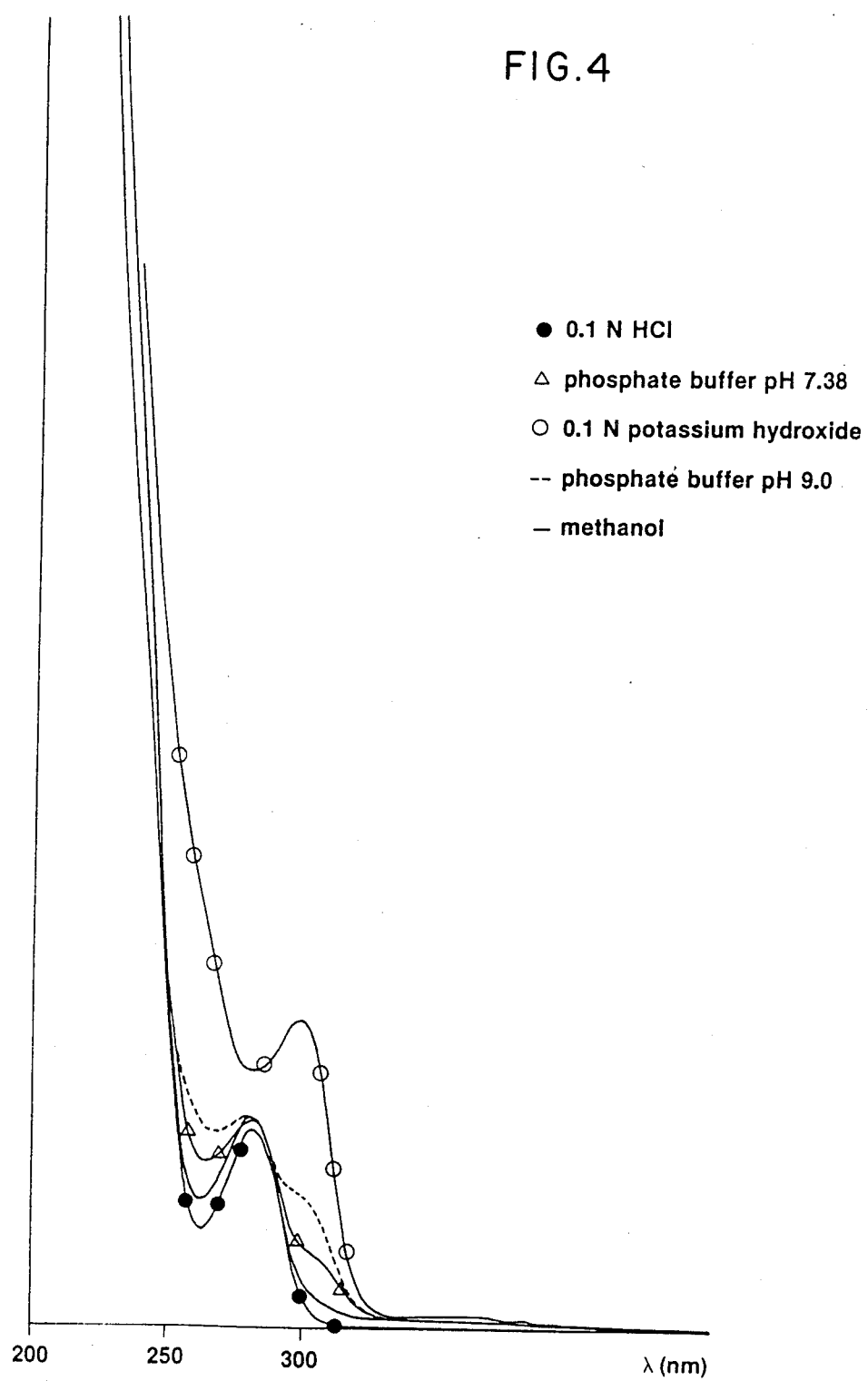

Physico-chemical characteristics of antibiotic A 40926 factor B (A) ultraviolet absorption spectrum, which is shown in FIG. 4 of the accompanying drawings, and exhibits the following absorption maxima:

|  | $\lambda$ max (nm) |
|---|---|
| (a) 0.1 N HCl | 282 |
| (b) phosphate buffer pH 7.38 | 281 |
|  | 300 (shoulder) |
| (c) 0.1 N sodium or potassium hydroxide | 300 |
| (d) phosphate buffer pH 9.0 | 283 |
|  | 300 (shoulder) |
| (e) methanol | 282 |

Figure 5:
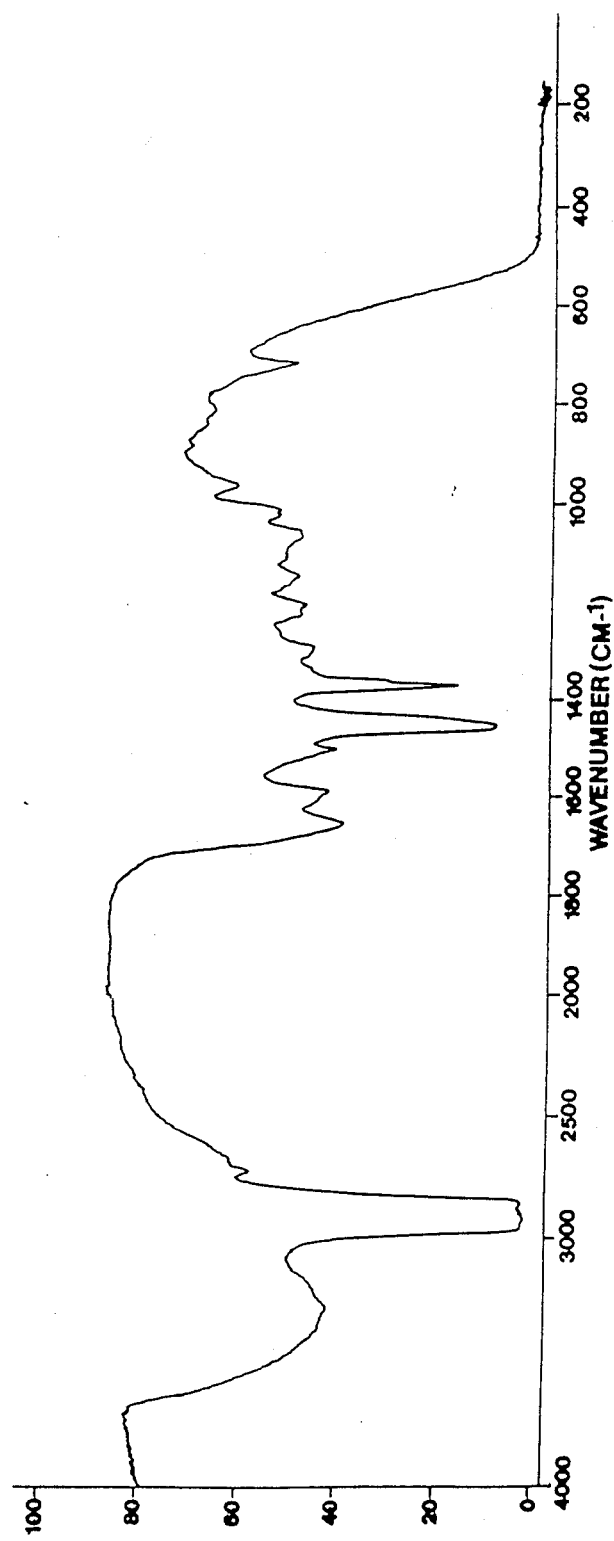

(B) infrared absorption spectrum which is shown in FIG. 5 of the accompanying drawings and exhibits the following absorption maxima (cm$^{-1}$): 3700–3080, 3080–2700 (nujol); 1720–1625; 1625–1560; 1505; 1460 (nujol); 1375 (nujol); 1295; 1230; 1210; 1150; 1100–1040; 1030; 1015; 970; 890; 840; 810; 720 (nujol).

Figure 6:
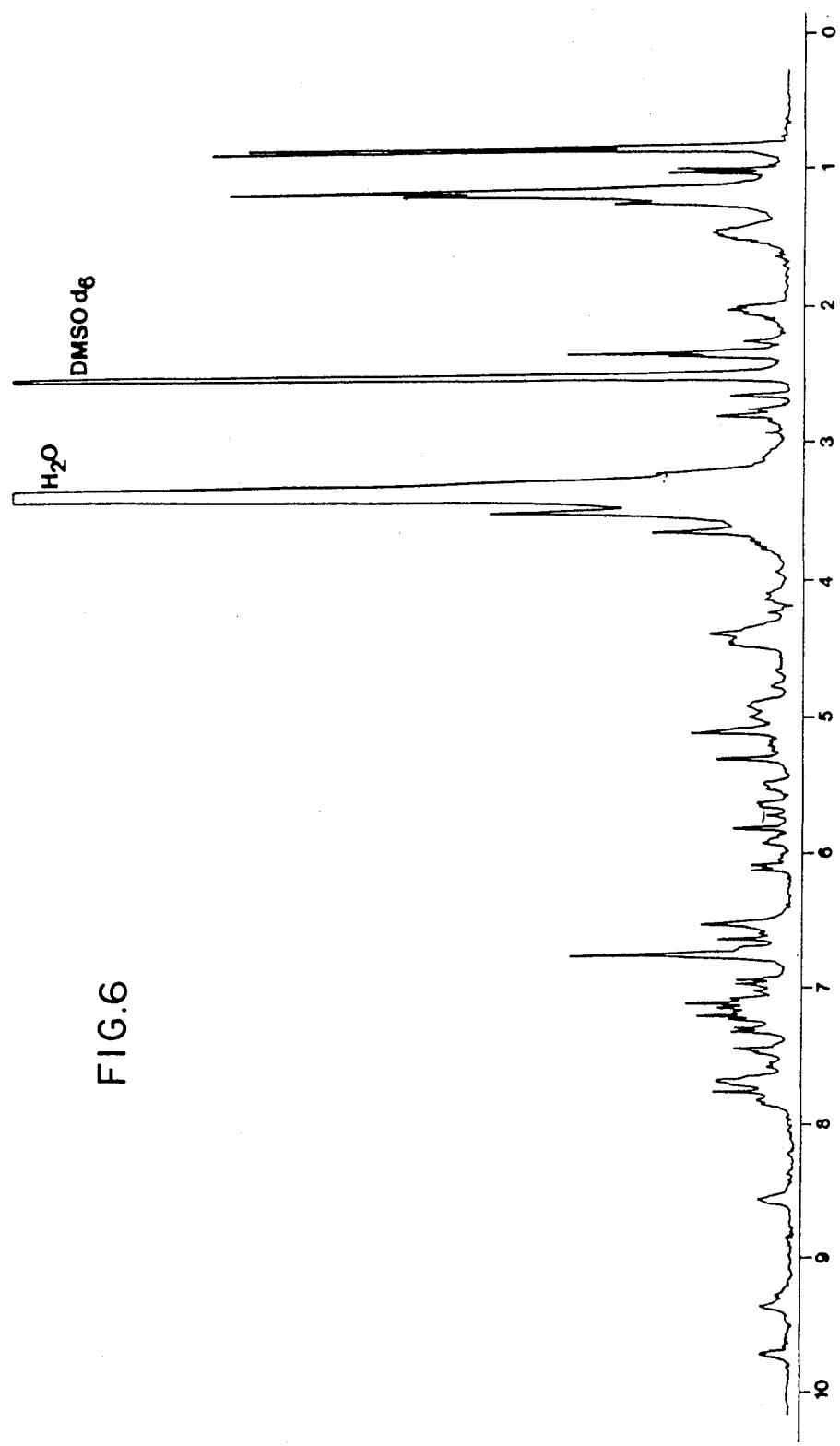

(C) $^1$H-NMR spectrum shown in FIG. 6 exhibits the following groups of signals (in ppm) in the 270 MHz $^1$H-NMR recorded in DMSO d$_6$ (hexadeuterodimethylsulfoxide) using TMS as the internal standard (0.00 ppm), ($\delta$=ppm): $\delta$ 0.85 (d, isopropyl CH$_3$'s); 1.15 ($\sim$13H); 1.44 ($\sim$2H); 2.02 (2H); 2.32–2.35 (3H); 4–6.1 ($\sim$16H); 6.1–8 ($\sim$23H); 8.52, 9.30, 9.68 (broad bands; mobile protons) 2.5–4 interference from H$_2$O peaks.

(D) Retention times (R$_t$) of 1.22 and 1.27 relative to Teicoplanin A$_2$ component 2 (R$_t$=20.3 min) when analyzed by reverse phase HPLC under the following conditions:

| column: | Ultrasphere ODS (5 $\mu$m) Altex (Beckman) 4.6 mm (i.d.) × 250 mm |
|---|---|
| pre-column: | Brownlee Labs RP 18 (5 $\mu$m) |
| eluent A: | CH$_3$CN 10% } adjusted |
|  | (2.5 g/l) NaH$_2$PO$_4$.H$_2$O 90% } at pH 6.0 |
| eluent B: | CH$_3$CN 70% } adjusted |
|  | (2.5 g/l) NaH$_2$PO$_4$.H$_2$O 30% } at pH 6.0 |
| elution: | linear gradient from 5% to 60% of eluent B in eluent A, in 40 min |
| flow rate: | 1.8 ml/min |
| U.V. detector: | 254 nm |
| internal standard: | Teicoplanin A$_2$ component 2 (Gruppo Lepetit S.p.A.) |

(E) elemental analysis, after the sample has been previously dried at about 140° C. under inert atmosphere ($\Delta$w 9.6%) indicates the following approximate percentage composition (average): carbon 54.09%; hydrogen 5.13%; nitrogen 6.34%; chlorine (total) 4.12%; chlorine (ionic) 0.39%. Inorganic residue at 900° C. in the air: 5%.

(F) acid base titration profile in 2-methoxyethanol (MCS):water, 4:1 upon titration with KOH after addition of an excess of HCl (pH 2.7) which indicates four ionizable functions having the following pk$_{MCS}$: 4.5, 5.6, 7.2, 9.2.

(G) R$_f$ value of 0.21 and a R$_f$ value relative to Teicoplanin A$_2$ component 2 of 0.53 in the following chromatographic system:

| 5% (w/v) aqueous Na$_2$SO$_4$ | 70 |
|---|---|

-continued

| | |
|---|---|
| acetonitrile | 30 | using silanized silica gel 60 $F_{254}$ Merck plates (layer thickness 0.25 mm)
Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using *B. subtilis* ATCC 6633 on minimal Davis medium.

(H) MW of about 1730 desumed from a FAB-MS spectrum showing the M+H$^⊕$ peak at 1731.

Physico-chemical characteristics of antibiotic A 40926 factor $B_0$ (A) ultraviolet absorption spectrum which is shown in FIG. 4 of the accompanying drawing and exhibits the following absorption maxima:

| | λ max (nm) |
|---|---|
| (a) 0.1 N HCl | 282 |
| (b) phosphate buffer pH 7.38 | 281 |
| | 300 (shoulder) |
| (c) 0.1 N sodium or potassium hydroxide | 300 |
| (d) phosphate buffer pH 9.0 | 283 |
| | 300 (shoulder) |
| (e) methanol | 282 |

(B) infrared absorption spectrum which shown in FIG. 5 of the accompanying drawings exhibits the following absorption maxima (cm$^{-1}$): 3700–3080, 3080–2700 (nujol); 1720–1625; 1625–1560; 1505; 1460 (nujol); 1375 (nujol); 1295; 1230; 1210; 1150; 1100–1040; 1030; 1015; 970; 890; 840; 810; 720 (nujol).

(C) $^1$H-NMR spectrum which shown in FIG. 6 exhibits the following groups of signals (in ppm) in the 270 MHz $^1$H-NMR recorded in DMSO $d_6$ (hexadeuterodimethylsulfoxide) using TMS as the internal standard (0.00 ppm), (δ=ppm): δ 0.85 (d, isopropyl CH$_3$'s); 1.15 (~13H); 1.44 (~2H); 2.02 (2H); 2.32–2.35 (3H); 4–6.1 (~16H); 6.1–8 (~23H); 8.52, 9.30, 9.68 (broad bands; mobile protons) 2.5–4 interference from H$_2$O peaks.

(D) Retention time ($R_t$) of 1.22 relative to Teicoplanin A$_2$ component 2 ($R_t$=20.3 min) when analyzed by reverse phase HPLC under the following conditions:

| column: | Ultrasphere ODS (5 μm) Altex (Beckman) 4.6 mm (i.d.) × 250 mm |
|---|---|
| pre-column: | Brownlee Labs RP 18 (5 μm) |
| eluent A: | CH$_3$CN 10% } adjusted |
| | (2.5 g/l) NaH$_2$PO$_4$.H$_2$O 90% } at pH 6.0 |
| eluent B: | CH$_3$CN 70% } adjusted |
| | (2.5 g/l) NaH$_2$PO$_4$.H$_2$O 30% } at pH 6.0 |
| elution: | linear gradient from 5% to 60% of eluent B in eluent A, in 40 min |
| flow rate: | 1.8 ml/min |
| U.V. detector: | 254 nm |
| internal standard: | Teicoplanin A$_2$ component 2 (Gruppo Lepetit S.p.A.) |

(E) elemental analysis, after the sample has been previously dried at about 140° C. under inert atmosphere (Δw 9.6%) indicates the following approximate percentage composition (average): carbon 54.09%; hydrogen 5.13%; nitrogen 6.34%; chlorine (total) 4.12%; chlorine (ionic) 0.39%. Inorganic residue at 900° C. in the air: 5%.

(F) acid base titration profile in 2-methoxyethanol (MCS):water, 4:1 upon titration with KOH after addition of an excess of HCl indicates four ionizable functions having the following pk$_{MCS}$: 4.5, 5.6, 7.2, 9.2.

(G) $R_f$ value of 0.21 and a $R_f$ value relative to Teicoplanin A$_2$ component 2 of 0.53 in the following chromatographic system:

| | |
|---|---|
| 5% (w/v) aqueous Na$_2$SO$_4$ | 70 |
| acetonitrile | 30 | using silanized silica gel 60 $F_{254}$ Merck plates (layer thickness 0.25 mm)
Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using *B. subtilis* ATCC 6633 on minimal Davis medium.

(H) MW of about 1730 desumed from a FAB-MS spectrum showing the M+H$^⊕$ peak at 1731.

Figure 7:
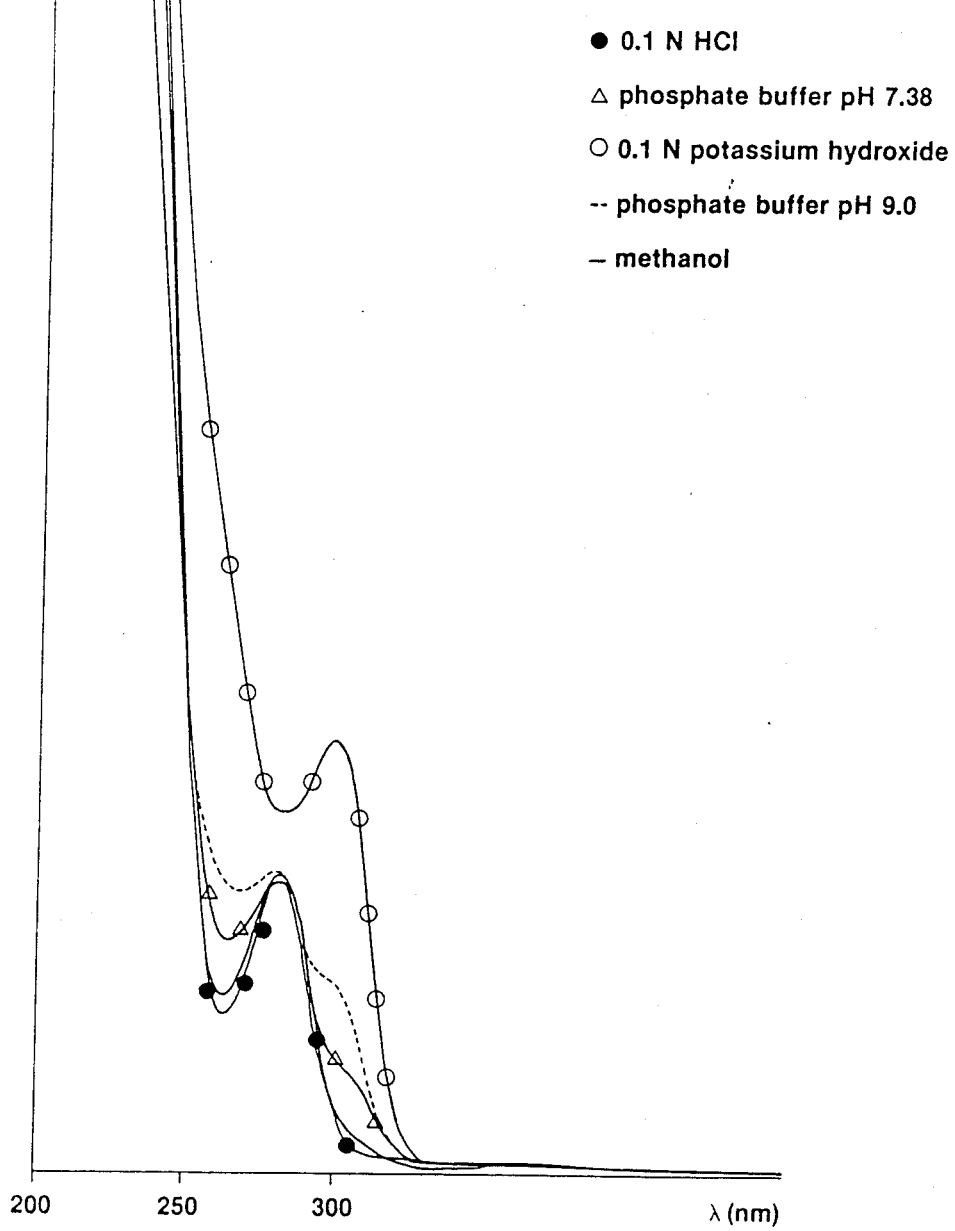

Physico-chemical characteristics of antibiotic A 40926 factor PA (A) ultraviolet absorption spectrum, shown in FIG. 7 of the accompanying drawings, exhibits the following absorption maxima:

| | λ max (nm) |
|---|---|
| (a) 0.1 N HCl | 282 |
| (b) 0.1 N potassium hydroxide | 300 |
| (c) phosphate buffer pH 7.38 | 282 |
| | 300 (shoulder) |
| (d) phosphate buffer pH 9.0 | 283 |
| | 300 (shoulder) |

Figure 8:
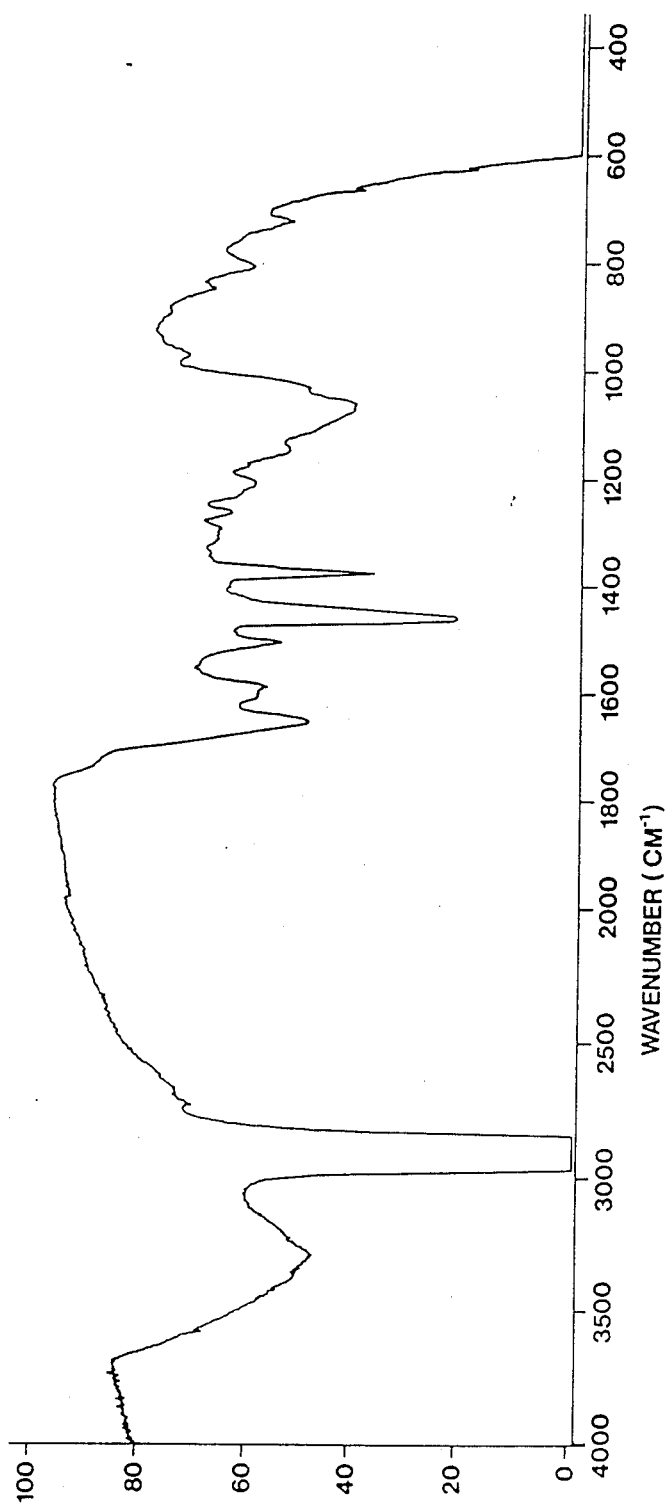

(B) infrared absorption spectrum shown in FIG. 8 of the accompanying drawings exhibits the following absorption maxima (cm$^{-1}$): 3700–3100, 3000–2800 (nujol); 1760–1710; 1655; 1620–1550; 1505; 1460 (nujol); 1375 (nujol); 1260, 1250–950; 845; 805; 720 (nujol).

Figure 9:
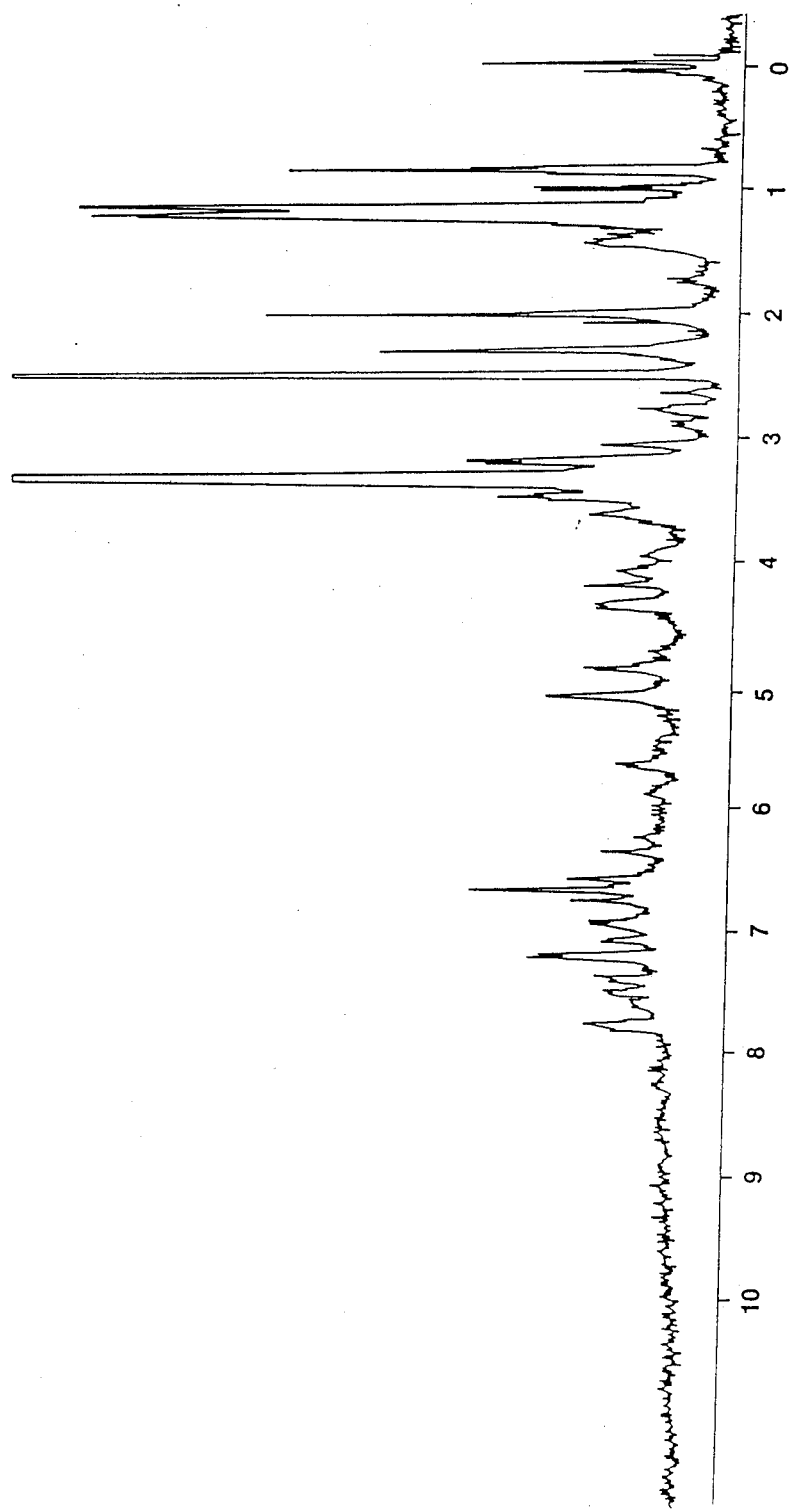

(C) $^1$H-NMR spectrum which is shown in FIG. 9 exhibits the following groups of signals (in ppm) in the 270 MHz $^1$H-NMR recorded in DMSO $d_6$ (hexadeuterodimethylsulfoxide) using TMS as the internal standard (0.00 ppm), (δ=ppm): 0.86, d's (CH$_3$); 1.15–1.22, m (CH$_2$)$_n$; 1.41, m (CH$_2$); 2.01, s (CH$_3$); 2.01, m (CH$_2$); 2.28, s (N-CH$_3$); 4.26–5.96, br (peptidic and aromatic CH's); 6.33–7.73 br (aromatic CH's and peptidic NH's).

br=broad
d=doublet
dd=doublet of doublets
m=multiplet
s=singlet
t=triplet (D) retention-time ($R_t$) of 1.15 relative to Teicoplanin A$_2$ component 2 ($R_t$=20.3 min) when analyzed by reverse phase HPLC under the following conditions:

| column: | Ultrasphere ODS (5 μm) Altex (Beckman) |

| pre-column: | 4.6 mm (i.d.) × 250 mm Brownlee Labs RP 18 (5 μm) | | |
|---|---|---|---|
| eluent A: | CH$_3$CN | 10% | adjusted at pH 6.0 |
| | (2.5 g/l) NaH$_2$PO$_4$.H$_2$O | 90% | |
| eluent B: | CH$_3$CN | 70% | adjusted at pH 6.0 |
| | (2.5 g/l) NaH$_2$PO$_4$.H$_2$O | 30% | |
| elution: | linear gradient from 5% to 60% of eluent B in eluent A, in 40 min | | |
| flow rate: | 1.8 ml/min | | |
| U.V. detector: | 254 nm | | |
| internal standard: | Teicoplanin A$_2$ component 2 (Gruppo Lepetit S.p.A.) | | |

(E) $R_f$ value relative to Teicoplanin A$_2$ component 2 of 0.62 in the following chromatographic system:

| 5% (w/v) aqueous Na$_2$SO$_4$ | 70 |
|---|---|
| acetonitrile | 30 | using silanized silica gel 60 F$_{254}$ Merck plates (layer thickness 0.25 mm)
Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using *B. subtilis* ATCC 6633 on minimal Davis medium.

(F) MW of about 1758 desumed from a FAB-MS spectrum showing a cluster of peaks having the most intense peak at 1761. The operative conditions of the FAB-MS analysis were the following:
Instrument: VG Mod ZAB SE equipped with FAB gun Ion Tech
Conditions:
Positive FAB, Xe
Accelerating voltage, 8 KV
Matrix: Thioglycerol-glycerol 1/1 (v/v).

Figure 10:
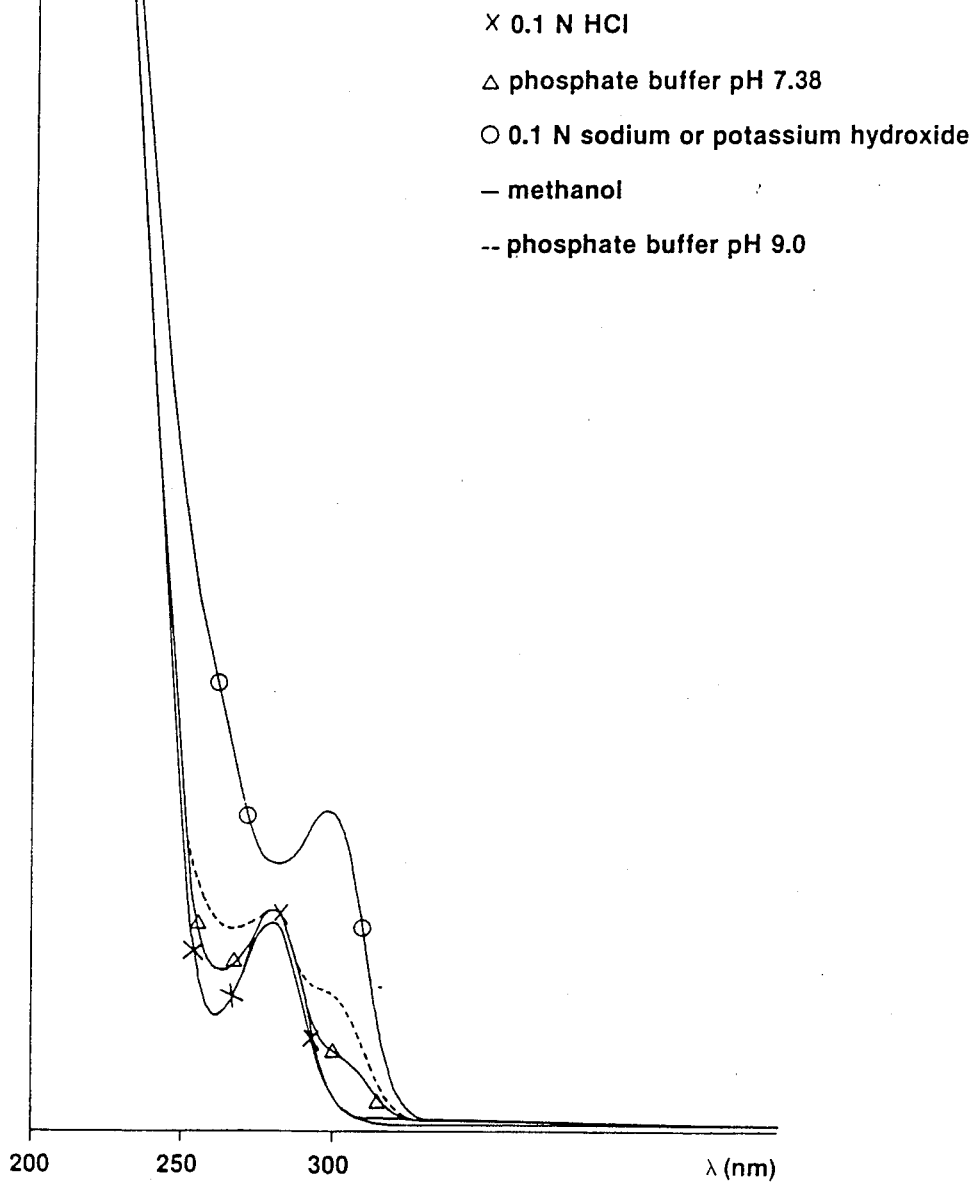

Physico-chemical characteristics of antibiotic A 40926 factor PB (A) ultraviolet absorption spectrum, shown in FIG. 10 of the accompanying drawings, exhibits the following absorption maxima:

| | | λ max (nm) |
|---|---|---|
| (a) | 0.1 N HCl | 282 |
| (b) | 0.1 N potassium hydroxide | 300 |
| (c) | phosphate buffer pH 7.38 | 282 |
| | | 300 (shoulder) |
| (d) | phosphate buffer pH 9.0 | 282 |
| | | 300 (shoulder) |

Figure 11:
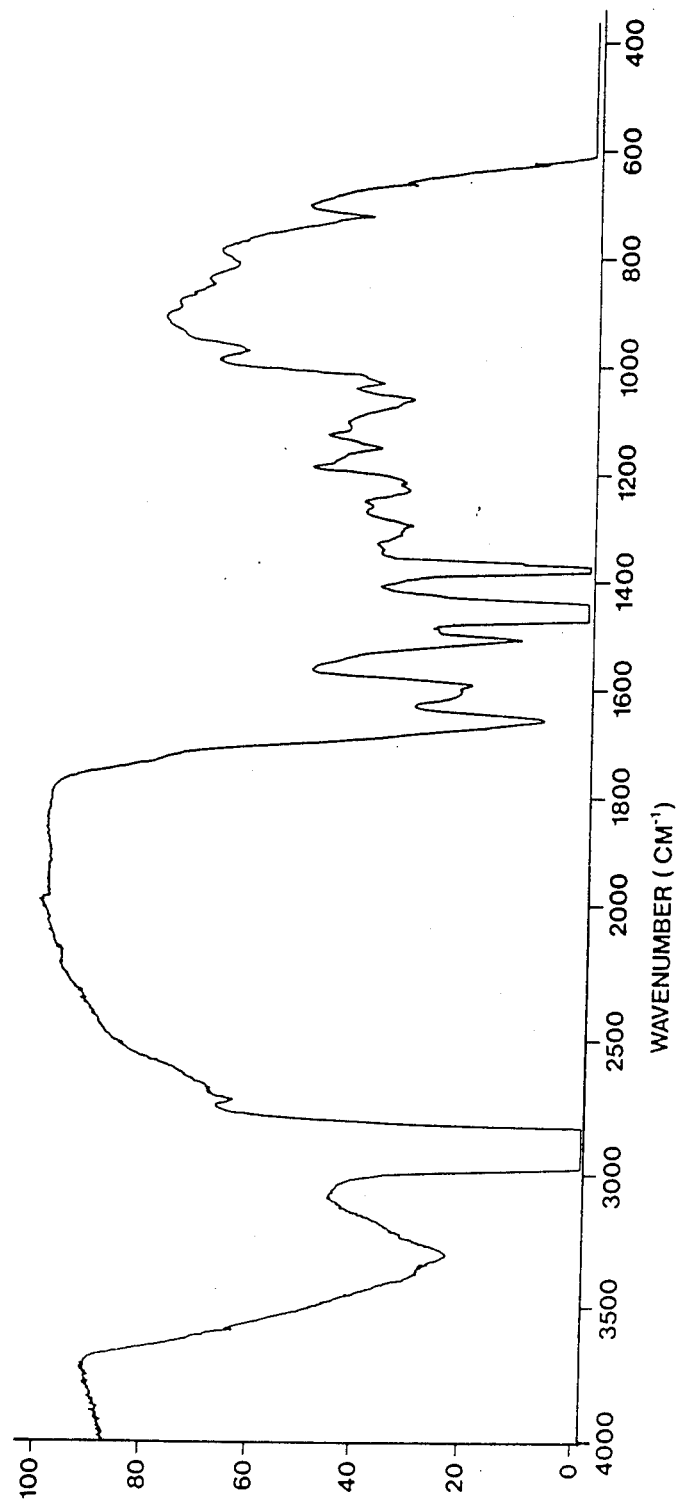

(B) infrared absorption spectrum which shown in FIG. 11 of the accompanying drawings exhibits the following absorption maxima (cm$^{-1}$): 3700–3100, 3000–2800 (nujol); 1760–1710; 1655; 1620–1560; 1605; 1480–1420 (nujol); 1375 (nujol); 1320–1270; 1230–1190; 1150; 1120–920; 845; 810; 720 (nujol).

Figure 12:
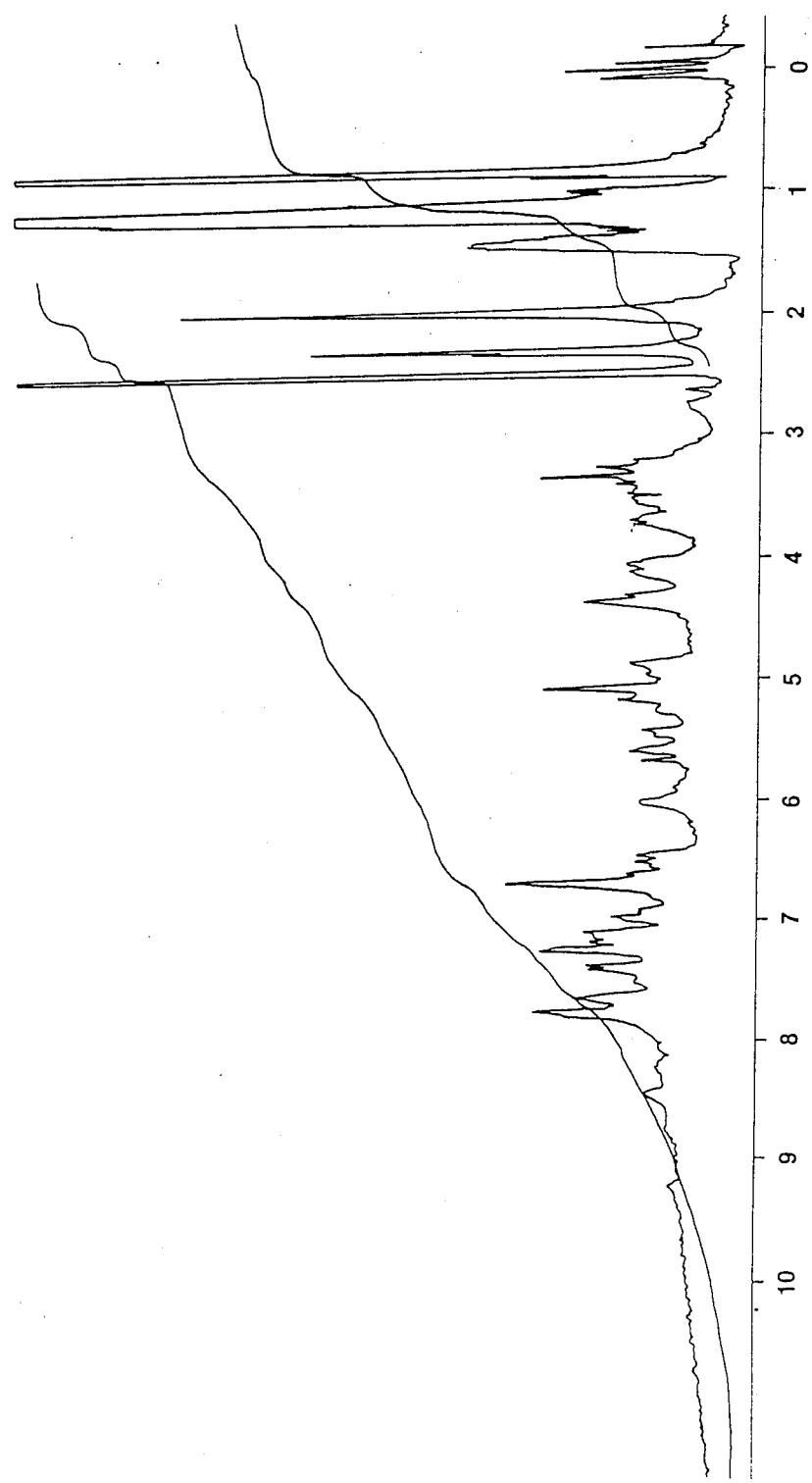

(C.1) $^1$H-NMR spectrum shown in FIG. 12 exhibits the following groups of signals (in ppm) at the 270 MHz in DMSO d$_6$ (hexadeuterodimethylsulfoxide) using TMS as the internal standard (0.00 ppm), (δ=ppm) multiplicity; (attribution): 0.84, d (isopropyl CH$_3$'s); 1.17, m (CH$_2$)$_n$; 1.43, m (CH$_2$), 1.99, s (CH$_3$); 2.01, m (CH$_2$); 2.31, s (N-CH$_3$); 2.79, dd (C-H); 3.70, m (C-H); 4.06–6.02, br (peptidic and aromatic CH's); 6.45–7.74, br (aromatic CH's and peptidic NH's); 8.19–9.99, br (peptidic NH's and phenolic OH's)

Figure 13:
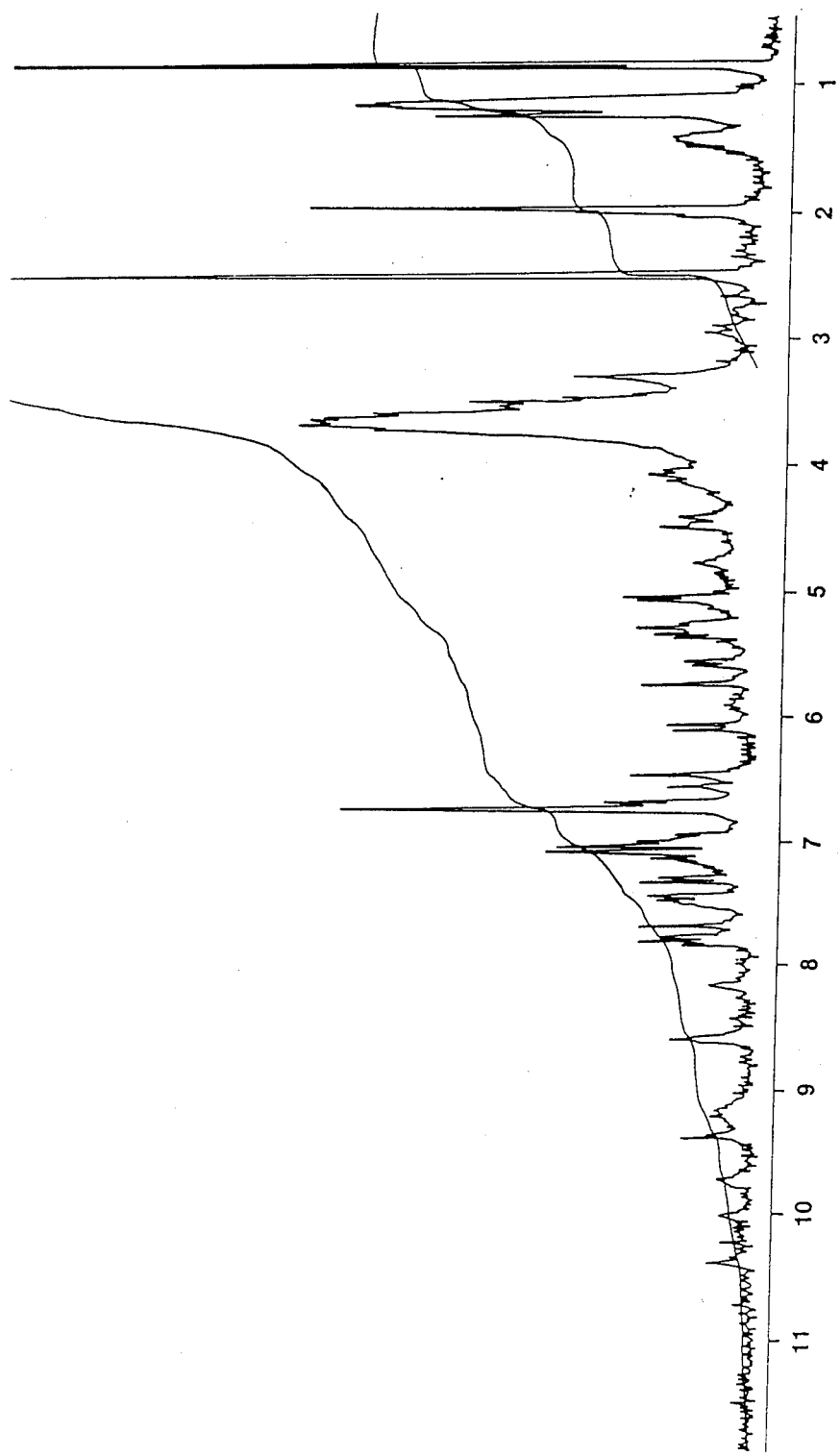

(C.2) $^1$H-NMR spectrum shown in FIG. 13 exhibits the following groups of signals (in ppm) at the 270 MHz in DMSO d$_6$ plus CF$_3$COOD using TMS as the internal standard (0.00 ppm), (δ=ppm) multiplicity; (attribution): 0.84, d (isopropyl CH$_3$'s); 1.13, m (CH$_2$)$_n$; 1.40, m (CH$_2$); 1.98, s (CH$_3$); 2.00, m (CH$_2$); 2.92, dd (C-H); 3.29–3.71, m (sugar C-H's); 4.07–6.09, s and m (peptidic and aromatic CH's); 6.45–7.83, s and m (aromatic CH's and peptidic NH's); 8.17–10.38 (peptidic NH's, phenolic OH's).

(D) retention times (R$_t$) of 1.27 and 1.32 relative to Teicoplanin A$_2$ component 2 (R$_t$=20.3 min) when analyzed by reverse phase HPLC under the following conditions:

| column: | Ultrasphere ODS (5 μm) Altex (Beckman) 4.6 mm (i.d.) × 250 mm | | |
|---|---|---|---|
| pre-column: | Brownlee Labs RP 18 (5 μm) | | |
| eluent A: | CH$_3$CN | 10% | adjusted at pH 6.0 |
| | (2.5 g/l) NaH$_2$PO$_4$.H$_2$O | 90% | |
| eluent B: | CH$_3$CN | 70% | adjusted at pH 6.0 |
| | (2.5 g/l) NaH$_2$PO$_4$.H$_2$O | 30% | |
| elution: | linear gradient from 5% to 60% of eluent B in eluent A, in 40 min | | |
| flow rate: | 1.8 ml/min | | |
| U.V. detector: | 254 nm | | |
| internal standard: | Teicoplanin A$_2$ component 2 (Gruppo Lepetit S.p.A.) | | |

(E) $R_f$ value relative to Teicoplanin A$_2$ component 2 of 0.53 in the following chromatographic system:

| 5% (w/v) aqueous Na$_2$SO$_4$ | 70 |
|---|---|
| acetonitrile | 30 | using silanized silica gel 60 F$_{254}$ Merck plates (layer thickness 0.25 mm)
Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using *B. subtilis* ATCC 6633 on minimal Davis medium.

(F) MW of about 1772 desumed from a FAB-MS spectrum showing a cluster of peaks having the most intense peak at 1776. The operative conditions of the FAB-MS analysis were the following:
Instrument: VG Mod ZAB SE equipped with FAB gun Ion Tech
Conditions:
Positive FAB, Xe
Accelerating voltage, 8 KV
Matrix: Thioglycerol-glycerol 1/1 (v/v).

The antibacterial activity of the compounds of the invention can be demonstrated in vitro by means of standard dilution tests on different microorganism cultures.

Culture media and growth conditions for MIC (minimal inhibitory concentration) determinations were as follows: Isosensitest broth (Oxoid), 24 h, for staphylococci, *Strep. faecalis* and Gram-negative bacteria (*Escherichia coli*, Pseudomonas, Proteus); Todd-Hewitt broth (Difco), 24 h for other streptococcal species; GC base broth (Difco)+1% Isovitalex (BBL), 48 h, $CO_2$-enriched atmosphere for *Neisseria gonorrhoeae*; GB base agar (Difco)+1% Isovitalex+0.001% hemin, 24 h for *Haemophilus influenzae*; AC broth (Difco), 24 h, anaerobic atmosphere for *Clostridium perfringens*; Wilkins-Chalgren agar (ref: T. D. Wilkins & S. Chalgren, 1976, Antimicrob. Ag. Chemother. 10, 926), 48 h, anaerobic atmosphere for the other anaerobes (*C. difficile, Propionibacterium acnes, Bacteroides fragilis*); PPLO broth (Difco)+10% horse serum+1% glucose, 48 h for *Mycoplasma gallisepticum*; Yeast nitrogen base broth (Difco), 24 h for *Candida albicans*. With the exception of *C. albicans* (30° C.), incubation was at 37° C. Inocula were as follows: 1% (v/v) of a 48 h broth culture for *M. gallisepticum*; about $10^4-10^5$ colony-forming units/ml for other broth dilution MICs; about $10^4-10^5$ bacteria/spot (inoculated with a multipoint inoculator) for agar dilution MICs (*H. influenzae, C. difficile, P. acnes, B. fragilis*).

subcutaneously with the test compound about 30 min after infection.

The $ED_{50}$ value was calculated on the 10th day by the method of Spearman and Karber (D. J. Finney "Statistical Methods in Biological Assay", Griffin, page 524, 1952) on the basis of the percentage of survival at each dose. In the above conditions the $ED_{50}$ for antibiotic A 40926 factor A was 0.47 mg/kg, for antibiotic A 40926 factor B was 0.33 mg/kg, for antibiotic A 40926 factor PA was 0.54 mg/kg and for antibiotic A 40926 factor PB 0.31 mg/kg.

The approximate acute toxicity in mice (i.p.) was evaluated according to methods known in the art. The approximate $LD_{50}$ of antibiotic A 40926 was found to be higher than 100 mg/kg in mice, when administered subcutaneously in mice.

Antibiotic A 40926 complex and its factors A, B, $B_0$, PA and PB are active against gram-positive bacteria which are responsible for many widely diffused infections. Because of the increasing resistance of these

TABLE IV

| Strain | Antibiotic A 40926 | | | |
|---|---|---|---|---|
| | Factor A | Factor B | Factor PA | Factor PB |
| | M.I.C. (µg/ml) | | | |
| Staph. aureus ATCC 6538 | 0.13 | 0.13 | | |
| Staph. aureus Tour (L165) $10^4$ cfu/ml | 0.13 | 0.13 | 0.5 | 1 |
| Staph. aureus Tour (L165) $10^6$ cfu/ml | 0.25 | 0.13 | 2 | 2 |
| Staph. epidermidis ATCC 12228 | | | 4 | 4 |
| Strept. mitis L 796 (clin. is.) | | | 0.06 | 0.06 |
| Strep. pyogenes C203 | 0.063 | 0.063 | 0.06 | 0.03 |
| Strep. pneumoniae UC41 | 0.063 | 0.063 | 0.06 | 0.06 |
| Strep. faecalis ATCC 7080 | 0.13 | 0.13 | 0.06 | 0.13 |
| Clostr. perfringens ISS 30543 | 0.016 | 0.016 | 0.008 | 0.008 |
| Clostr. difficile ATCC 9689 | 0.25 | 0.13 | 0.25 | 0.13 |
| Propion. acne ATCC 6919 | 0.03 | 0.016 | 0.03 | 0.03 |
| Neisseria gonorrhoeae L 997 (clin. isol.) | 1 | 0.5 | 4 | 2 |
| Haemophilus influenzae ATCC 19418 | 64 | 64 | 64 | 64 |
| Proteus vulgaris X19H ATCC 881 | >128 | >128 | >128 | >128 |
| Escherichia coli SKF 12140 | >128 | >128 | >128 | >128 |
| Pseudomonas aeruginosa ATCC 10145 | >128 | >128 | >128 | >128 |
| Bacteroides fragilis ATCC 23745 | 64 | 64 | 64 | 64 |
| Candida albicans SKF 2270 | >128 | >128 | | |
| Mycoplasma gallisepticum Weybridge | 64 | 64 | 128 | 64 |

TABLE V

| | Bactericidal effect on *N. gonorrhoeae* strains | | | |
|---|---|---|---|---|
| N. gonorrhoeae | Antibiotic A 40926 complex | | Spectinomycin | |
| | | | MIC | MBC |
| Strain | MIC (48 h) | MBC (24 h) | (48 h) | (24 h) |
| L 1001 * | 1 | 1 | 16 | 32 |
| L 1004 * | 1 | 0.5 | 16 | 32 |
| L 1007 (CTC 6820) | 2 | 2 | 16 | 16 |
| L 1596 ** | 2 | 2 | >128 | >128 |
| L 1601 *** | 1 | 1 | 16 | 16 |
| L 1605 *** | 2 | 2 | 32 | 32 |

MIC = minimal inhibitory concentration
MBC = minimal bactericidal concentration (lowest concentration at which 99.9% of the initial inoculum is killed within the indicated time)
* = clinical isolate
** = clinical isolate, spectinomycin-resistant
*** = clinical isolate, penicillin-resistant The antimicrobial activity of the compounds of the invention is confirmed also in in vivo experiments conducted essentially as described by R. Pallanza et al., J. Antimicrob. Chemother. 11, 419 (1983). The experimental infection was induced in mice by intraperitoneally administering a suspension of *S. pyogenes* C 203. Inocula had been adjusted so that the untreated animals died of septicemia within 48 h. Animals were treated pathogens to the usual therapeutic treatments, the need for new antibiotic substances is still great.

As already stated, the antibiotic substances of the invention possess a good activity against Neisseria strains, such as *Neisseria gonorrhoeae*, while they are practically inactive against other gram-negative bacteria.

It is known that the incidence of gonorrhea has risen steadily in the last 15–20 years.

The control of the infection is at present troublesome because of the high number of re-infections which is related also to the behaviour of infected individuals who do not take the necessary care in avoiding the transmission of the disease for the whole duration of the infection. On the other hand, there is an increasing resistance of the causative organism to the commonly used antibiotics so that new associations of antibiotics and longer treatments become necessary. Therefore there is an increasing need for new antibiotic substances which might be effective in curing gonococcal infections, and in particular *Neisseria gonorrhoeae* infections, with a limited number of administrations, or even with a single dose administration.

In general for antibacterial treatment antibiotic A 40926 complex, one of its factors A, B, $B_0$, PA and PB as well as the non-toxic pharmaceutically acceptable salts thereof or mixture thereof, can be administered by different routes such as topically or parenterally. The parenteral administration is, in general, the preferred route of administration.

Compositions for injection may take such forms as suspensions, solutions, or emulsions in oily or aqueous vehicles, and may contain adjuvants such as suspending, stabilizing and/or dispersing agents.

Alternatively, the active ingredient may be in powder form for reconstitution at the time of delivery when a suitable vehicle, such as sterile water, is added thereto.

Depending on the route of administration, these compounds can be formulated into various dosage forms.

In some instances, it may be possible to formulate the compounds of the invention in enteric-coated dosage forms for oral administration which may be prepared as known in the art (see for instance "Remington's Pharmaceutical Sciences", fifteenth edition, Mack Publishing Company, Easton, Pennsylvania, U.S.A., page 1614).

This could be especially the case when the absorption of the antimicrobial substance in the enteric tract is particularly desired while passing unaltered through the gastric tract.

The amount of active principle to be administered depends on various factors such as the size and condition of the subject to be treated, the route and frequency of administration, and the causative agent involved.

The antibiotic substances of the present invention, namely antibiotic A 40926 complex, its factors A, PA, B, $B_0$ and PB, and the physiologically acceptable salts thereof, are generally effective at a daily dosage of between about 0.5 and 50 mg of active ingredient per kilo of patient body weight, optionally divided into 1 to 4 administrations per day.

Particularly desirable compositions are those prepared in dosage units containing from about 100 to about 5,000 mg per unit.

However, when used in the single-dose treatment of gonorrhea, higher minimum doses of antibiotic A 40926 complex, its factors A, PA, B, $B_0$ or PB, generally ranging between 0.5 and 50 mg/Kg, should be employed in order to maintain an effective blood level of the drug over an extended period of time.

Furthermore, in the treatment of gonorrhea, a sustained-action parenteral dosage form is preferably employed. Sustained-action formulations can be prepared based on different mechanisms and methods, as known in the art.

A preferred method for preparing a sustained-action formulation containing antibiotic A 40926 complex, its factors A, B, $B_0$, PA and PB involves the use of a water insoluble form of this antibiotic suspended in an aqueous or oily medium.

These forms, i.e. either as an insoluble salt or as the free acid, in fact, are released very slowly upon intramuscular injection, because of their low water-solubility, thus giving substained blood levels of the antibiotic substance.

Preparation of pharmaceutical compositions:

A unit dosage form for intramuscular injection is prepared with 5 ml of sterile suspension USP containing 8% propylene glycol and 1,000 mg of antibiotic A 40926 factor A.

A unit dosage form for intramuscular injection is prepared with 5 ml of sterile suspension USP containing 8% propylene glycol and 500 mg of antibiotic A 40926 factor B.

A unit dosage form for intramuscular injection is prepared with 2,000 mg of antibiotic A 40926 factor B sodium salt suspended in 5 ml of sterile water for injection.

Furthermore, the antibiotics of the invention are useful for suppressing the growth of *Clostridium difficile* which causes pseudomembranous colitis in the intestine. The antibiotic could be used in the treatment of pseudomembranous colitis by the oral administration of an effective dose of the antibiotic or a pharmaceutically-acceptable salt thereof, prepared in a pharmaceutically-acceptable dosage form. For such use, the antibiotic can be administered in gelatin capsules or in liquid suspension.

Besides their activity as medicaments, the compounds of the present invention can be used as animal growth promoters.

For this purpose, one or more of the compounds of the invention is administered orally in a suitable feed. The exact concentration employed is that which is required to provide for the active agent in a growth promotant effective amount when normal amounts of feed are consumed.

The addition of the active compounds of the invention to animal feed is preferably accomplished by preparing an appropriate feed premix containing the active compounds in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and CO., S. Francisco, U.S.A., 1969 or "Livestock Feeds and Feeding" O and B books, Corvallis, Oregon, U.S.A., 1977) and are incorporated herein by reference.

The following Examples further illustrate the invention and, as such, should not be construed as limiting its scope.

EXAMPLE 1:

Fermentation of Actinomadura sp. ATCC 39727

A culture of antibiotic A 40926 producing strain (Actinomadura sp. ATCC 39727) is grown on oatmeal agar slant for 2-3 weeks at 28° C. and used to inoculate a 500 ml Erlenmeyer flask containing 100 ml of medium composed of 0.5% meat extract, 0.5% autolyzed yeast, 0.5% peptone, 0.3% casein hydrolyzed, 2% glucose, 0.15% NaCl (pH 7.5 before sterilization).

The flask is incubated at 28° C. on a rotary shaker at 200 rpm for about 72 h and then the culture is transferred to a fermentor containing 4 l of the above medium. This culture is grown at 28° C. for about 72 h with air-flow of about two liters per minute and stirring at about 900 rpm. Then, it is used to inoculate a 200 l fermentor of the same medium. This fermentor is aerated with 100 l per minute of sterile air and is stirred at 250 rpm at about 28° C. The antibiotic production is monitored by the paper-disc agar diffusion method using *B. subtilis* on a minimal medium as the test organism. The maximum activity is obtained after 72-96 h.

EXAMPLE 2:

Recovery of antibiotic A 40926

(A) The fermentation broth is cooled to 4° C., brought to pH 9.5 and stirred. After about 1 h it is filtered and the filtrate is adjusted to pH about 3.5 with an aqueous mineral acid. The mixture is stirred for 30 min at 4° C. and then filtered with (Hyflo-FloMa ®) filter aid. The clear filtrate is discharged and the filter cake is suspended in deionized water, adjusted to pH about 8.5, stirred and then filtered. The recovered cake is subjected to the same procedure. The pooled filtrates contain antibiotic A 40926.

(B) Swollen D-Ala-D-Ala-$\epsilon$-aminocaproyl-Sepharose modified matrix (2 l) is added to the fermentation broth obtained according to Example 1 (after filtering it and bringing the pH of the clear filtrate to about 8.5) or to the pooled filtrate obtained according to the above Example 2 A. After stirring overnight at room temperature, the resin is recovered by filtration and is washed sequentially with about 2×10 l of 0.45 mM HCl-TRIS buffer pH 7.5 (TRIS=2-amino-2-hydroxymethyl-1,3-propanediol) which contains 5% (w/v) NaCl and then with distilled water (4×20 l).

The A 40926 antibiotic is eluted from the resin with 1% (w/v) ammonia hydrate (2×10 l). The eluates are left overnight at room temperature and then concentrated to a small volume (about 2.5 l). Water is eliminated by azeotropical distillation with n-butanol. Petroleum ether is then added, precipitating 3.4 g of crude antibiotic A 40926 complex.

EXAMPLE 3:

Purification of antibiotic A 40926 complex AB

Crude antibiotic A 40926 complex obtained essentially following the procedure of the above Example 2, (750 mg; HPLC titre 70%) is dissolved in 400 ml of water, adjusted to pH 7.5 and filtered. The filtrate is then subjected to affinity chromatography on a D-Ala-D-Ala-$\epsilon$-aminocaproyl-Sepharose column (50 ml of swollen resin; bed height=5 cm). The column, equilibrated with 0.16% (w/v) ammonia containing 2M NaCl adjusted to pH 7.5 with HCl, is developed sequentally with the following three buffer solutions:

buffer A: 0.16% (w/v) ammonia containing 2M NaCl adjusted to pH 7.5 with HCl, (2.6 column bed volumes);
buffer B: 0.16% (w/v) ammonia containing 2M NaCl adjusted to pH 9.5 with HCl (16 column bed volumes);
buffer C: 1% (w/v) aqueous ammonia pH 11.4 (2.6 column bed volumes).

Buffer C elutes antibiotic A 40926 complex AB in a single fraction. This eluted fraction is adjusted to pH 7.0 and reapplied to the same affinity column buffered with with 10 mM TRIS-HCl pH 7.0. The column is washed with distilled water until desalting is complete. The antibiotic is then eluted with 2 column bed volumes of 0.39% (w/v) aqueous ammonia pH 11.0.

The eluted fractions are concentrated to a small aqueous mixture and then freeze-dried. Pure antibiotic A 40926 complex AB (374 mg) is obtained.

EXAMPLE 4:

Isolation of antibiotic A 40926 factor A and B (A) Antibiotic A 40926 complex as obtained according to Example 2 (3.3 g) or antibiotic A 40926 complex AB as obtained according to Example 3 (2.3 g) is suspended in 0.5 l of water, stirred and then filtered. The clear filtrate is applied to a silanized silica gel column (200 g; bed h 18 cm; silanized Silica gel 60; 70–230 mesh, Merck Inc.) pre-equilibrated with solution A (0.001M aqueous sodium EDTA containing 0.25% (w/v) NaH$_2$PO$_4$.H$_2$O and 2.5% (w/v) NaCl adjusted to pH 6.0 with NaOH). The column is eluted with a linear gradient from 0% to 40% (v/v) of acetonitrile in solution A with a total volume of about 7 l in about 48 h. Fractions of about 15.5 ml are collected and assayed by bioassay on *Bacillus subtilis* and analyzed by HPLC. Fractions having a similar antibiotic content are pooled. Fractions No. 310–330 and No. 348–365 contained the antibiotic substances denominated, respectively, A 40926 factor A and A 40926 factor B.

(B) The pooled fractions containing the single A 40926 factors A and B are concentrated under reduced pressure to remove acetonitrile, diluted with water (about twice the volume of the initial solutions) and applied to a silanized silica gel column of the type described above (volume of the swollen matrix: 50 ml; bed height of 15 cm). The column is washed with deionized water until desalting is complete and finally developed with acetonitrile/water 60:40 (v/v).

The eluted fractions are concentrated under reduced pressure and the residues are freeze-dried to obtain 134 mg of antibiotic A 40926 from the first group of eluted fractions (fractions 310–330 above) and 206 mg of A 40926 factor B from the second group of eluted fractions (fractions 348–365, above).

EXAMPLE 5:

Isolation of antibiotic A 40926 factor PA and factor PB

By essentially following the procedure of Example 2A and the first steps of the procedure of Example 2B, the antibiotic linked to the resin is eluted with 1% (w/v) ammonia hydrate (2×20 l). The eluates are adjusted to pH 7.8 with sulfuric acid and concentrated to a small volume under vacuum by azeotropical distillation with n-butanol to obtain an aqueous concentrate which is then filtered on paper. The recovered filtrate contains antibiotic A 40926 factor PA, A 40926 factor PB and minor amounts of A 40926 factor A and factor B (HPLC). A sample (10 ml) of this aqueous concentrate containing about 50 mg/ml of pure antibiotic A 40926 complex (HPLC analysis) is filtered on 5 micrometer pore-size filter (Acrodisc ®; Gelman Science Inc.) and then applied to a stainless steel column (diameter=2 cm) containing 20 g of an octadecyl silyl reverse-phase silica gel (Lichrisorb RP 18, Merck Inc.; particle size 10 $\mu$m). The silica gel is then packed under moderate pressure (nominal pressure about 14 bar) in a stainless steel column of a Chromatospac Modulprep apparatus (Yoben Yvon, France) and equilibrated with a mixture consisting of acetonitrile and 18 mM sodium phosphate buffer pH 6.0), 25:75 (v/v). The elution is carried out using the same solvent mixture used for the equilibration at a flow rate of about 10.5 ml/min. The eluate is monitored by bioassay on *Bacillus subtilis* and by HPLC.

Those fractions having similar antibiotic content are pooled and the homogeneous fractions of 5 chromatographic runs are concentrated to evaporate the organic solvent.

The resulting solution is diluted with aqueous 1M sodium chloride to twice the original volume and is applied to a silanized silica gel column (50 g; bed height 5 cm; Silanized silica gel 60; Merck Inc.) equilibrated with water.

The column is washed with deionized water until desalting is complete (no AgCl precipitation in the eluates after addition of aqueous $AgNO_3$) and then eluted with acetonitrile:water 1:1 (v/v). The eluates having similar antibiotic content (HPLC analysis) are pooled, concentrated to a small volume by azeotropical distillation with n-butanol to obtain an aqueous phase which is then freeze-dried. Yields:

antibiotic A 40926 factor PA: 55 mg
antibiotic A 40926 factor PB: 51 mg
antibiotic A 40926 factor A: 38 mg
antibiotic A 40926 factor $B_0$: 33 mg

EXAMPLE 6:

Alternative method for isolating antibiotic A 40926 factor B

The pooled concentrate of two preparations made according to Example 2 (the last step) is filtered and the filtrate is applied to a silanized silica gel chromatographic column; (400 g; bed h 30 cm; Silicagel 60, 70–230 mesh, Merck Inc.) pre-equilibrated with water.

The column is rinsed with water (6 l) and the adsorbed antibiotic is eluted with acetonitrile/water according to the following sequence:

2.7 l 5% (v/v) acetonitrile in water
1.6 l 10% (v/v) acetonitrile in water
2.9 7 l 15% (v/v) acetonitrile in water
3.1 5 l 20% (v/v) acetonitrile in water Fractions of about 18 ml are collected. The activity of the eluted fractions is tested by paper-disc bioassay on susceptible microorganisms such as *B. subtilis* and analyzed by HPLC. Fractions with similar antibiotic content are pooled (fractions 472–526) and concentrated under reduced pressure. n-Butanol is added to this concentrate to azeotropically remove water. The butanolic solution which remains is in turn concentrated to a small volume to precipitate antibiotic A 40926 factor B (1.4 g). This product is washed with petroleum ether under stirring and collected by filtration (three times). Upon drying under vacuum 760 mg of A 40926 factor B are obtained.

By resubmitting antibiotic A 40926 factor B to the above column chromatography a product (540 mg) antibiotic A 40926 factor $B_0$ is obtained which has the same physico-chemical characteristics reported above for antibiotic A 40926 factor B except that it shows only a peak at HPLC analysis, namely the peak with retention time of 1.22 relative to Teicoplanin $A_2$ component 2.

EXAMPLE 7:

Transformation of antibiotic A 40926 factor PA and antibiotic A 40926 factor PB into antibiotic A 40926 factor A and factor B, respectively Antibiotic A 40926 factor PA and antibiotic A 40926 factor PB (50 mg) are separately dissolved in 2.5 ml of aqueous 1% (w/v) $NH_4OH$ and the resulting solutions are kept for about 24 h at room temperature with stirring. Antibiotic A 40926 factor A is obtained from the solution originally containing antibiotic A 40926 factor PA, and antibiotic A 40926 factor B is obtained from the solution originally containing antibiotic A 40926 factor PB by removing water by azeotropic distillation with n-butanol, precipitating with ethyl ether and collecting the precipitate by filtration (yield about 75%).

Preparation of D-Ala-D-Ala-Sepharose

Activated CH-Sepharose 4B (Pharmacia Fine Chemicals) (1 g) is swollen for 15 minutes in 1 mM cold ice hydrochloric acid and washed with the same solution. The obtained gel (about 3 ml) is mixed with a solution of D-alanyl-D-alanine (30 mg) in 0.5M sodium chloride and 0.1M sodium bicarbonate buffer at pH 8.

The mixture is rotated end-over-end for 1 hour at room temperature.

After the coupling reaction is completed, the ligand excess is washed off with the buffer. The unlinked activated groups of the dextrane support are blocked by treating them with 1M ethanolamine hydrochloride at pH 9 for 1 hour.

The the Sephadex-ε-aminocaproyl-D-alanyl-D-alanine modified matrix is recovered by filtration and thoroughly washed alternatively with 0.5M sodium chloride and 0.1M sodium acetate pH 4, and with 0.5M sodium chloride and 0.1M tris(hydroxymethyl)aminomethane buffer pH 8. (four times).

We claim:

1. An antibiotic substance selected from the group consisting of antibiotic A 40926 complex of the antibiotics below, antibiotic A 40926 factor A, antibiotic A 40926 factor B, antibiotic A 40926 factor $B_0$, antibiotic A 40926 factor PA, antibiotic A 40926 factor PB, a mixture thereof and the addition salts thereof which are characterized as following:

Antibiotic A 40926 factor A in the non-salt form:

(A) ultraviolet absorption spectrum which exhibits the following absorption maxima:

|     |                                    | λ max (nm)         |
| --- | ---------------------------------- | ------------------ |
| (a) | 0.1 N HCl                          | 281                |
| (b) | phosphate buffer pH 7.38           | 281                |
|     |                                    | 300 (shoulder)     |
| (c) | 0.1 N sodium or potassium hydroxide | 300               |
| (d) | methanol                           | 282                |
| (e) | phosphate buffer pH 9.0            | 282                |
|     |                                    | 300 (shoulder)     |

(B) infrared absorption spectrum which exhibits the following absorption maxima ($cm^{-1}$): 3700–3100, 3100–2800 (nujol); 1655; 1620–1560; 1510; 1480–1410 (nujol); 1375 (nujol); 1320–1250; 1250–1190; 1100–950; 845; 810; 720 (nujol);

(C) $^1$H-NMR spectrum which exhibits the following groups of signals (in ppm) at 270 MHz recorded in DMSO $d_6$ (hexadeuterodimethylsulfoxide) using TMS as the internal standard (0.00 ppm), (δ=ppm): δ 0.86 (t's, 6H); 1.21 (~11H); 1.43 (2H); 2.01 (2H); 2.31–2.34 (3H); 4–6.2 (~16H); 6.2–8 (~23H); 8.44, 9.22, 9.66 (broad bands; mobile protons) 2.5–4: interference from $H_2O$ peaks;

(D) retention-time ($R_t$) of 1.22 relative to Teicoplanin $A_2$ component 2 ($R_t$=20.3 min), when analyzed by reverse phase HPLC under the following conditions:

| column:      | Ultrasphere ODS (5 μm) Altex (Beckman) 4.6 mm (i.d.) × 250 mm |
| ------------ | ------------------------------------------------------------- |
| pre-column:  | Brownlee Labs RP 18 (5 μm)                                    |
| eluent A:    | $CH_3CN$   10%   ⎫ adjusted                                   |

-continued

|  |  |  |  |
|---|---|---|---|
|  | (2.5 g/l) NaH$_2$PO$_4$.H$_2$O | 90% | at pH 6.0 |
| eluent B: | CH$_3$CN | 70% | adjusted |
|  | (2.5 g/l) NaH$_2$PO$_4$.H$_2$O | 30% | pH 6.0 |
| elution: | linear gradient from 5% to 60% of eluent B in eluent A, in 40 min | | |
| flow rate: | 1.8 ml/min | | |
| U.V. detector: | 254 nm | | |
| internal standard: | Teicoplanin A$_2$ component 2 (Gruppo Lepetit S.p.A.) | | |

Under the same conditions the retention time relative to Testosterone (Roussel Uclaf) is 0.60;

(E) elemental analysis, after the sample has been previously dried at about 140° C. under inert atmosphere ($\Delta$w 4.6%) which indicates the following approximate percentage composition (average): carbon 55.82%; hydrogen 5.17%; nitrogen 6.31%; chlorine (total) 4.24%; chlorine (ionic) 0.37%. Inorganic residue at 900° C. in the air: 1.2%;

(F) acid-base titration profile in 2-methoxyethanol (MCS):water, 4:1 upon titration with KOH after addition of an excess of HCl which indicates four ionizable functions having the following pk$_{MCS}$: 4.6, 5.6, 7.2, 9.2;

(G) R$_f$ value of 0.24 and a R$_f$ value relative to Teicoplanin A$_2$ component 2 of 0.70 in the following chromatographic system:

| | |
|---|---|
| 5% (w/v) aqueous Na$_2$SO$_4$ | 70 |
| acetonitrile | 30 | using silanized silica gel 60 F$_{254}$ Merck plates (layer thickness 0.25 mm)
Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using *B. subtilis* ATCC 6633 on minimal Davis medium;

(H) MW of about 1716 desumed from a FAB-MS spectrum showing the M+H$^\oplus$ peak at 1717;

Antibiotic A 40926 factor B in the non-salt form (A) ultraviolet absorption spectrum which exhibits the following absorption maxima:

|  |  | $\lambda$ max (nm) |
|---|---|---|
| (a) | 0.1 N HCl | 282 |
| (b) | phosphate buffer pH 7.38 | 281 |
|  |  | 300 (shoulder) |
| (c) | 0.1 N sodium or potassium hydroxide | 300 |
| (d) | phosphate buffer pH 9.0 | 283 |
|  |  | 300 (shoulder) |
| (e) | methanol | 282 |

(B) infrared absorption spectrum which exhibits the following absorption maxima (cm$^{-1}$): 3700–3080, 3080–2700 (nujol); 1720–1625; 1625–1560; 1505; 1460 (nujol); 1375 (nujol); 1295; 1230; 1210; 1150; 1100–1040; 1030; 1015; 970; 890; 840; 810; 720 (nujol);

(C) $^1$H-NMR spectrum which exhibits the following groups of signals (in ppm) in the 270 MHz $^1$H-NMR recorded in DMSO d$_6$ (hexadeuterodimethylsulfoxide) using TMS as the internal standard (0.00 ppm), ($\delta$=ppm): $\delta$ 0.85 (d, isopropyl CH$_3$'s); 1.15 (~13H); 1.44 (~2H); 2.02 (2H); 2.32–2.35 (3H); 4–6.1 (~16H); 6.1–8 (~23H); 8.52, 9.30, 9.68 (broad bands; mobile protons) 2.5–4 interference from H$_2$O peaks;

(D) Retention times (R$_t$) of 1.22 and 1.27 relative to Teicoplanin A$_2$ component 2 (R$_t$=20.3 min) when analyzed by reverse phase HPLC under the following conditions:

|  |  |  |  |
|---|---|---|---|
| column: | Ultrasphere ODS (5 $\mu$m) Altex (Beckman) 4.6 mm (i.d.) × 250 mm | | |
| pre-column: | Brownlee Labs RP 18 (5 $\mu$m) | | |
| eluent A: | CH$_3$CN | 10% | adjusted |
|  | (2.5 g/l) NaH$_2$PO$_4$.H$_2$O | 90% | at pH 6.0 |
| eluent B: | CH$_3$CN | 70% | adjusted |
|  | (2.5 g/l) NaH$_2$PO$_4$.H$_2$O | 30% | at pH 6.0 |
| elution: | linear gradient from 5% to 60% of eluent B in eluent A, in 40 min | | |
| flow rate: | 1.8 ml/min | | |
| U.V. detector: | 254 nm | | |
| internal standard: | Teicoplanin A$_2$ component 2 (Gruppo Lepetit S.p.A.) | | |

(E) elemental analysis, after the sample has been previously dried at about 140° C. under inert atmosphere ($\Delta$w 9.6%) indicates the following approximate percentage composition (average): carbon 54.09%; hydrogen 5.13%; nitrogen 6.34%; chlorine (total) 4.12%; chlorine (ionic) 0.39%; inorganic residue at 900° C. in the air: 5%;

(F) acid base titration profile in 2-methoxyethanol (MCS):water, 4:1 upon titration with KOH after addition of an excess of HCl (pH 2.7) which indicates four ionizable functions having the following pk$_{MCS}$: 4.5, 5.6, 7.2, 9.2;

(G) R$_f$ value of 0.21 and a R$_f$ value relative to Teicoplanin A$_2$ component 2 of 0.53 in the following chromatographic system:

| | |
|---|---|
| 5% (w/v) aqueous N$_2$SO$_4$ | 70 |
| acetonitrile | 30 | using silanized silica gel 60 F$_{254}$ Merck plates (layer thickness 0.25 mm)
Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using *B. subtilis* ATCC 6633 on minimal Davis medium;

(H) MW of about 1730 desumed from a FAB-MS spectrum showing the M+H$^\oplus$ peak at 1731;

Antibiotic A 40926 factor B$_0$ in the non-salt form (A) ultraviolet absorption spectrum which exhibits the following absorption maxima:

|  |  | $\lambda$ max (nm) |
|---|---|---|
| (a) | 0.1 N HCl | 282 |
| (b) | phosphate buffer pH 7.38 | 281 |
|  |  | 300 (shoulder) |
| (c) | 0.1 N sodium or potassium hydroxide | 300 |
| (d) | phosphate buffer pH 9.0 | 283 |
|  |  | 300 (shoulder) |

| | | λ max (nm) |
|---|---|---|
| (e) | methanol | 282 |

(B) infrared absorption spectrum which exhibits the following absorption maxima (cm$^{-1}$): 3700–3080, 3080–2700 (nujol); 1720–1625; 1625–1560; 1505; 1460 (nujol); 1375 (nujol); 1295; 1230; 1210; 1150; 1100–1040; 1030; 1015; 970; 890; 840; 810; 720 (nujol);

(C) $^1$H-NMR spectrum which exhibits the following groups of signals (in ppm) in the 270 MHz $^1$H-NMR recorded in DMSO d$_6$ (hexadeuterodimethylsulfoxide) using TMS as the internal standard (0.00 ppm), (δ=ppm): δ 0.85 (d, isopropyl CH$_3$'s); 1.15 (~13H); 1.44 (~2H); 2.02 (2H); 2.32–2.35 (3H); 4–6.1 (~16H); 6.1–8 (~23H); 8.52, 9.30, 9.68 (broad bands; mobile protons) 2.5–4 interference from H$_2$O peaks;

(D) Retention time (R$_t$) of 1.22 relative to Teicoplanin A$_2$ component 2 (R$_t$=20.3 min) when analyzed by reverse phase HPLC under the following conditions:

| column: | Ultrasphere ODS (5 μm) Altex (Beckman) 4.6 mm (i.d.) × 250 mm | | |
|---|---|---|---|
| pre-column: | Brownlee Labs RP 18 (5 μm) | | |
| eluent A: | CH$_3$CN | 10% | adjusted at pH 6.0 |
| | (2.5 g/l) NaH$_2$PO$_4$.H$_2$O | 90% | |
| eluent B: | CH$_3$CN | 70% | adjusted at pH 6.0 |
| | (2.5 g/l) NaH$_2$PO$_4$.H$_2$O | 30% | |
| elution: | linear gradient from 5% to 60% of eluent B in eluent A, in 40 min | | |
| flow rate: | 1.8 ml/min | | |
| U.V. detector: | 254 nm | | |
| internal standard: | Teicoplanin A$_2$ component 2 (Gruppo Lepetit S.p.A.) | | |

(E) elemental analysis, after the sample has been previously dried at about 140° C. under inert atmosphere (Δw 9.6%) indicates the following approximate percentage composition (average): carbon 54.09%; hydrogen 5.13%; nitrogen 6.34%; chlorine (total) 4.12%; chlorine (ionic) 0.39%; inorganic residue at 900° C. in the air: 5%;

(F) acid base titration profile in 2-methoxyethanol (MCS):water, 4:1 upon titration with KOH after addition of an excess of HCl indicates four ionizable functions having the following pk$_{MCS}$: 4.5, 5.6, 7.2, 9.2;

(G) R$_f$ value of 0.21 and a R$_f$ value relative to Teicoplanin A$_2$ component 2 of 0.53 in the following chromatographic system:

| 5% (w/v) aqueous Na$_2$SO$_4$ | 70 |
|---|---|
| acetonitrile | 30 | using silanized silica gel 60 F$_{254}$ Merck plates (layer thickness 0.25 mm)
Visualization:
U.V. light
Yellow color with Pauly Reagent, i.e. diazotized sulfanilic acid (J. Chromatog. 20, 171 (1965), Z. Physiol. Chem. 292, 99, (1953))

Bioautography using *B. subtilis* ATCC 6633 on minimal Davis medium;
(H) MW of about 1730 desumed from a FAB-MS spectrum showing the M+H$^⊕$ peak at 1731;

Antibiotic A 40926 factor PA in the non-salt form:
(A) An ultraviolet absorption spectrum which exhibits the following absorption maxima:

| | | λ max (nm) |
|---|---|---|
| (a) | 0.1 N HCl | 282 |
| (b) | 0.1 N potassium hydroxide | 300 |
| (c) | phosphate buffer pH 7.38 | 282 |
| | | 300 (shoulder) |
| (d) | phosphate buffer pH 9.0 | 283 |
| | | 300 (shoulder) |

(B) infrared absorption spectrum which exhibits the following absorption maxima (cm$^{-1}$): 3700–3100, 3000–2800 (nujol); 1760–1710; 1655; 1620–1550; 1505; 1460 (nujol); 1375 (nujol); 1260, 1250–950; 845; 805; 720 (nujol);

(C) $^1$H-NMR spectrum which exhibits the following groups of signals (in ppm) in the 270 MHz $^1$H-NMR recorded in DMSO d$_6$ (hexadeuterodimethylsulfoxide) using TMS as the internal standard (0.00 ppm), (δ=ppm): 0.86, d's (CH$_3$); 1.15–1.22, m (CH$_2$)$_n$; 1.41, m (CH$_2$); 2.01, s (CH$_3$); 2.01, m (CH$_2$); 2.28, s (N-CH$_3$); 4.26–5.96, br (peptidic and aromatic CH's); 6.33–7.73 br (aromatic CH's and peptidic NH's):
br=broad
d=doublet
dd=doublet of doublets
m=multiplet
s=singlet
t=triplet (D) retention time (R$_t$) of 1.15 relative to Teicoplanin A$_2$ component 2 (R$_t$=20.3 min) when analyzed by reverse phase HPLC under the following conditions:

| column: | Ultrasphere ODS (5 μm) Altex (Beckman) 4.6 mm (i.d.) × 250 mm | | |
|---|---|---|---|
| pre-column: | Brownlee Labs RP 18 (5 μm) | | |
| eluent A: | CH$_3$CN | 10% | adjusted at pH 6.0 |
| | (2.5 g/l) NaH$_2$PO$_4$.H$_2$O | 90% | |
| eluent B: | CH$_3$CN | 70% | adjusted at pH 6.0 |
| | (2.5 g/l) NaH$_2$PO$_4$.H$_2$O | 30% | |
| elution: | linear gradient from 5% to 60% of eluent B in eluent A, in 40 min | | |
| flow rate: | 1.8 ml/min | | |
| U.V. detector: | 254 nm | | |
| internal standard: | Teicoplanin A$_2$ component 2 (Gruppo Lepetit S.p.A.) | | |

(E) R$_f$ value relative to Teicoplanin A$_2$ component 2 of 0.62 in the following chromatographic system:

| 5% (w/v) aqueous Na$_2$SO$_4$ | 70 |
|---|---|
| acetonitrile | 30 | using silanized silica gel 60 F$_{254}$ Merck plates (layer thickness 0.25 mm)
Visualization:
U.V. light Yellow color with Pauly Reagent, i.e. diazotized sulfanilic acid (J. Chromatog. 20, 171 (1965), Z. Physiol. Chem. 292, 99, (1953))
Bioautography using *B. subtilis* ATCC 6633 on minimal Davis medium;

(F) MW of about 1758 desumed from a FAB-MS spectrum showing a cluster of peaks having the most intense peak at 1761; the operative conditions of the FAB-MS analysis were the following:
Instrument: VG Mod ZAB SE equipped with FAB gun Ion Tech
Conditions:
Positive FAB, Xe
Accelerating voltage, 8 KV
Matrix: Thioglycerol-glycerol 1/1 (v/v);

Antibiotic A 40926 factor PB in the non-salt form:

(A) An ultraviolet absorption spectrum which exhibits the following absorption maxima:

|     |                         | $\lambda$ max (nm) |
| --- | ----------------------- | ------------------ |
| (a) | 0.1 N HCl               | 282                |
| (b) | 0.1 N potassium hydroxide | 300              |
| (c) | phosphate buffer pH 7.38 | 282               |
|     |                         | 300 (shoulder)     |
| (d) | phosphate buffer pH 9.0 | 282                |
|     |                         | 300 (shoulder)     |

(B) infrared absorption spectrum which exhibits the following absorption maxima ($cm^{-1}$): 3700–3100, 3000–2800 (nujol); 1760–1710; 1655; 1620–1560; 1605; 1480–1420 (nujol); 1375 (nujol); 1320–1270; 1230–1190; 1150, 1120–920; 845; 810; 720 (nujol);

(C.1) $^1$H-NMR spectrum which exhibits the following groups of signals (in ppm) at the 270 MHz in DMSO $d_6$ (hexadeuterodimethylsulfoxide) using TMS as the internal standard (0.00 ppm), ($\delta$=ppm) multiplicity; (attribution): 0.84, d (isopropyl $CH_3$'s); 1.17, m $(CH_2)_n$; 1.43, m $(CH_2)$, 1.99, s $(CH_3)$; 2.01, m $(CH_2)$; 2.31, s (N-$CH_3$); 2.79, dd (C-H); 3.70, m (C-H); 4.06–6.02, br (peptidic and aromatic CH's); 6.45–7.74, br (aromatic CH's and peptidic NH's); 8.19–9.99, br (peptidic NH's and phenolic OH's);

(c.2) $^1$H-NMR spectrum which exhibits the following groups of signals (in ppm) at the 270 MHz in DMSO $d_6$ plus $CF_3COOD$ using TMS as the internal standard (0.00 ppm), ($\delta$=ppm) multiplicity; (attribution): 0.84, d (isopropyl $CH_3$'s); 1.13, m $(CH_2)_n$; 1.40, m $(CH_2)$; 1.98, s $(CH_3)$; 2.00, m $(CH_2)$; 2.92, dd (C-H); 3.29–3.71, m (sugar C-H's); 4.07–6.09, s and m (peptidic and aromatic CH's); 6.45–7.83, s and m (aromatic CH's and peptidic NH's); 8.17–10.38 (peptidic NH's, phenolic OH's);

(D) retention times ($R_t$) of 1.27 and 1.32 relative to Teicoplanin $A_2$ component 2 ($R_t$=20.3 min) when analyzed by reverse phase HPLC under the following conditions:

| column:      | Ultrasphere ODS (5 μm) Altex (Beckman) 4.6 mm (i.d.) × 250 mm |         |                  |
| ------------ | ------------------------------------------------------------- | ------- | ---------------- |
| pre-column:  | Brownlee Labs RP 18 (5 μm)                                    |         |                  |
| eluent A:    | $CH_3CN$                                                      | 10%     | adjusted at pH 6.0 |
|              | (2.5 g/l) $NaH_2PO_4 \cdot H_2O$                              | 90%     |                  |
| eluent B:    | $CH_3CN$                                                      | 70%     | adjusted at pH 6.0 |
|              | (2.5 g/l) $NaH_2PO_4 \cdot H_2O$                              | 30%     |                  |
| elution:     | linear gradient from 5% to 60% of eluent B in eluent A, in 40 min |   |                  |

-continued

| flow rate:         | 1.8 ml/min                                         |
| ------------------ | -------------------------------------------------- |
| U.V. detector:     | 254 nm                                             |
| internal standard: | Teicoplanin $A_2$ component 2 (Gruppo Lepetit S.p.A.) |

(E) $R_f$ value relative to Teicoplanin $A_2$ component 2 of 0.53 in the following chromatographic system:

| 5% (w/v) aqueous $Na_2SO_4$ | 70 |
| --------------------------- | -- |
| acetonitrile                | 30 | using silanized silica gel 60 $F_{254}$ Merck plates (layer thickness 0.25 mm)
Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using *B. subtilis* ATCC 6633 on minimal Davis medium;

(F) MW of about 1772 desumed from a FAB-MS spectrum showing a cluster of peaks having the most intense peak at 1776; the operative conditions of the FAB-MS analysis were the following:
Instrument: VG Mod ZAB SE equipped with FAB gun Ion Tech
Conditions:
Positive FAB, Xe
Accelerating voltage, 8 KV
Matrix: Thioglycerol-glycerol 1/1 (v/v).

2. A process for producing an antibiotic substance of claim 1 which comprises cultivating the strain *Actinomadura sp.* ATCC 39727, or an antibiotic A 40926-producing mutant or variant thereof, under submerged aerobic conditions, in an aqueous nutrient medium containing assimilable sources of carbon, nitrogen, and inorganic salts until substantial A 40926 complex activity is imparted to the culture medium, filtering the fermentation medium, extracting the A 40926 complex from the filtrate, causing the A 40926 complex to precipitate from the extract, and isolating factors PA, PB, A, B, and Bo from the A 40926 complex via silica gel chromatography.

3. A process as in claim 2 wherein the strain is cultivated at a temperature between 20° C. and 40° C.

4. A process as in claim 2 wherein the temperature is between 24° C. and 35° C.

5. A process as in claim 2 wherein the recovery and isolation of the antibiotic substances is obtained by submitting the filtered fermentation broth to an affinity chromatography on immobilized D-Alanyl-Alanine followed by partition, reverse-phase or ion-exchange chromatography.

6. A process according to claim 2 wherein the recovery of the antibiotic substances includes:
(a) submitting the fermentation broth to affinity chromatography on immobilized D-Alanyl-D-Alanine
(b) rapidly neutralizing the pooled antibiotic containing eluted fractions and
(c) if isolation of the pure individual factors is desired, isolating the antibiotic A 40926 factors PA, PB, A, B and Bo by means of reverse-phase liquid chromatography on silanized silica gel.

7. A process according to claim 2 for preparing a compound selected from antibiotic A 40926 complex, antibiotic A 40926 factor A, antibiotic A 40926 factor B, and antibiotic A 40926 factor $B_0$ which comprises:

(a) making the fermentation mass basic at a pH between 8.5 and 10.5
(b) filtering
(c) acidifying the clear filtrate to pH 2.5–4.5
(d) filtering and discharging the filtrate
(e) suspending the filter cake in water and making it basic at a pH between 8 and 9
(f) after recovering the crude antibiotic A 40926 complex by filtration, subjecting it to affinity chromatography on immobilized D-Alanyl-D-Alanine
(g) if isolation of antibiotic A 40926 factor A or factor B is desired, isolating antibiotic A 40926 factor A and factor B by means of partition, reverse-phase or ion-exchange chromatography, and
(h) subjecting antibiotic A 40926 factor B to a further affinity chromatography procedure when antibiotic A 40926 factor $B_0$ is desired.

8. A process according to claim 7 wherein the chromatographic technique is reverse-phase chromatography and the stationary phase is selected from silanized silica gel and non-functionalized polystyrene resins.

9. A process according to claim 7 wherein the stationary phase is silanized silica gel pre-equilibrated with a buffered solution at a pH between 4 and 9 and the eluent is a linear gradient mixture of a polar water-miscible solvent in the same buffered solution.

10. A method of treating bacterial infections in a patient in need thereof which comprises administering to said patient an effective amount of antibiotic A 40926 complex, antibiotic A 40926 factor A, antibiotic A 40926 factor B, antibiotic A 40926 factor $B_0$, antibiotic A 40926 factor PA, antibiotic A 40926 factor PB, a mixture thereof or an addition salt thereof, as defined in claim 1.

11. A method of claim 10 wherein the bacterial infection is an infection of a gram positive bacteria.

12. A method of claim 10 wherein the bacterial infection is an infection of a Neisseria genus bacteria.

13. A method of claim 10 wherein the bacterial infection is an infection of *Neisseria gonorrhoeae* bacteria.

14. A method of claim 10 wherein the bacterial infection is an infection of Clostridium genus bacteria.

15. A method of claim 10 wherein the bacterial infection is an infection of *Clostridium difficule* bacteria.

16. An antibacterially effective pharmaceutical composition which comprises an effective amount of an antibiotic substance of claim 1 in admixture with a pharmaceutically acceptable vehicle.

* * * * *